United States Patent
Levinson

(10) Patent No.: US 6,217,590 B1
(45) Date of Patent: *Apr. 17, 2001

(54) SURGICAL INSTRUMENT FOR APPLYING MULTIPLE STAPLES AND CUTTING BLOOD VESSELS AND ORGANIC STRUCTURES AND METHOD THEREFOR

(75) Inventor: Melvin E. Levinson, Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/354,008

(22) Filed: Jul. 15, 1999

Related U.S. Application Data

(63) Continuation-in-part of application No. 09/235,412, filed on Jan. 22, 1999.

(51) Int. Cl.$^7$ .................................................. A61B 17/10
(52) U.S. Cl. ........................... 606/142; 606/139; 606/158
(58) Field of Search .................................. 606/139, 142, 606/151, 157, 158

(56) References Cited

U.S. PATENT DOCUMENTS

| | | |
|---|---|---|
| 3,326,216 | 6/1967 | Wood . |
| 3,631,707 | 1/1972 | Miller . |
| 3,665,924 | 5/1972 | Noiles et al. . |
| 3,675,688 | 7/1972 | Bryan et al. . |
| 3,713,533 | 1/1973 | Reimels . |
| 3,735,762 | 5/1973 | Bryan et al. . |
| 3,740,994 | 6/1973 | De Carlos , Jr. . |
| 3,777,538 | 12/1973 | Weatherly et al. . |
| 3,819,100 | 6/1974 | Noiles et al. . |
| 3,867,944 | 2/1975 | Samuels . |
| 3,955,581 | 5/1976 | Spasiano et al. . |
| 4,076,120 | 2/1978 | Carroll et al. . |
| 4,086,926 | 5/1978 | Green et al. . |
| 4,146,130 | 3/1979 | Samuels et al. . |

(List continued on next page.)

OTHER PUBLICATIONS

Ethicon Endo_Surgery Tool Product Spec. Sheets, Circa 1998 Richard Wolf Product Brochure, p. 1, CIRCA 1998.

Stor F Sinus Instrument Product Brochure, CIRCA 1998 Circon Reposable Laparoscopic Instrument Product Spec. Sheets pp. 205,208 CIRCA 1998.

Snowden–Pencer Endoscopic Plastic Surgery Product Spec. p. 5, CIRCA 1998 CIT GmbH and for Endoscopic Instrument, CIRCA 1998.

Scion Surgical Instruments, CIRCA 1998 Scion Endoscopic and Instrument Brochures, CIRCa 1998.

*Primary Examiner*—Glenn K. Dawson
(74) *Attorney, Agent, or Firm*—Robert C. Kain, Jr.

(57) ABSTRACT

A surgical instrument for stapling and cutting a blood vessel or other organic structure utilizes at least two surgical staple clips. The surgical instrument in one embodiment includes an elongated tube with a longitudinally movable rod disposed therein. A handle, mounted on a proximal end of the tube, includes a movable member which causes the movable rod to move longitudinally. In one embodiment, a pair of surgical staple clip carrying jaw sets are pivotally mounted on a common lateral axis located at the distal end of the elongated tube, each clip jaw set includes at least two jaw members, and each jaw member defines a clip action cam following channel. In a further embodiment, jaw members are ganged together and move as a unit based upon a cam follower surface motivated by a cam actuator member. In a different embodiment with more than eight clip carrying jaws the cam follower channels or surfaces have substantially different shapes such that different clips close on the blood vessel or organic structure at different rates and at different times with respect to the longitudinal position of the movable rod.

30 Claims, 17 Drawing Sheets

U.S. PATENT DOCUMENTS

| | | |
|---|---|---|
| 4,188,953 | 2/1980 | Klieman et al. . |
| 4,449,530 | 5/1984 | Bendel et al. . |
| 4,602,629 | 7/1986 | Schirman . |
| 4,696,396 | 9/1987 | Samuels . |
| 4,844,066 | 7/1989 | Stein . |
| 4,971,198 | 11/1990 | Mericle . |
| 5,032,127 | 7/1991 | Frazee et al. ............ 606/143 |
| 5,049,152 | 9/1991 | Simon et al. . |
| 5,104,394 | 4/1992 | Knoerfler .................. 606/143 |
| 5,171,250 | 12/1992 | Yoon . |
| 5,192,288 | 3/1993 | Thompson et al. ........ 606/143 |
| 5,269,792 | 12/1993 | Kovac et al. .............. 606/158 |
| 5,336,229 | 8/1994 | Noda ......................... 606/144 |
| 5,447,513 | 9/1995 | Davidson et al. .......... 606/143 |
| 5,527,319 | 6/1996 | Green et al. ............... 606/143 |
| 5,542,949 * | 8/1996 | Yoon .......................... 606/142 |
| 5,601,573 | 2/1997 | Fogelberg et al. ......... 606/143 |
| 5,676,672 * | 10/1997 | Watson et al. ............. 606/120 |
| 5,709,706 * | 1/1998 | Kienzle et al. ............. 606/142 |
| 5,925,052 * | 7/1999 | Simmons .................... 606/120 |

* cited by examiner

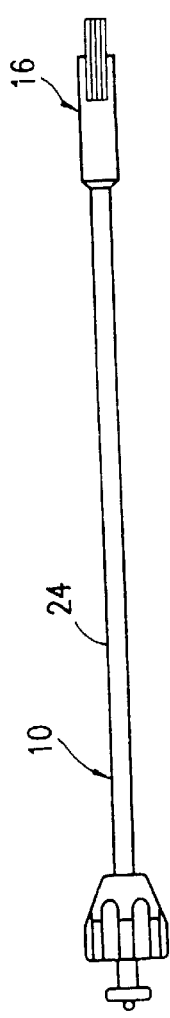
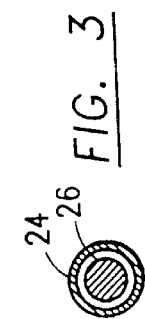
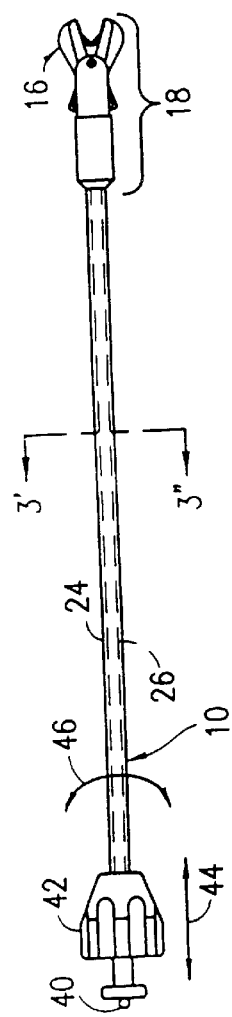
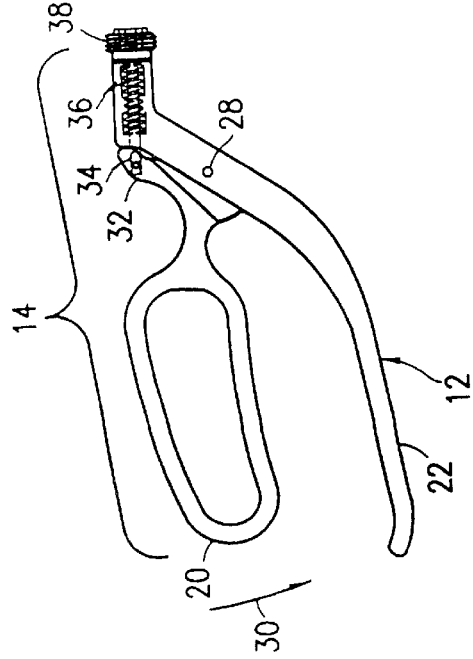

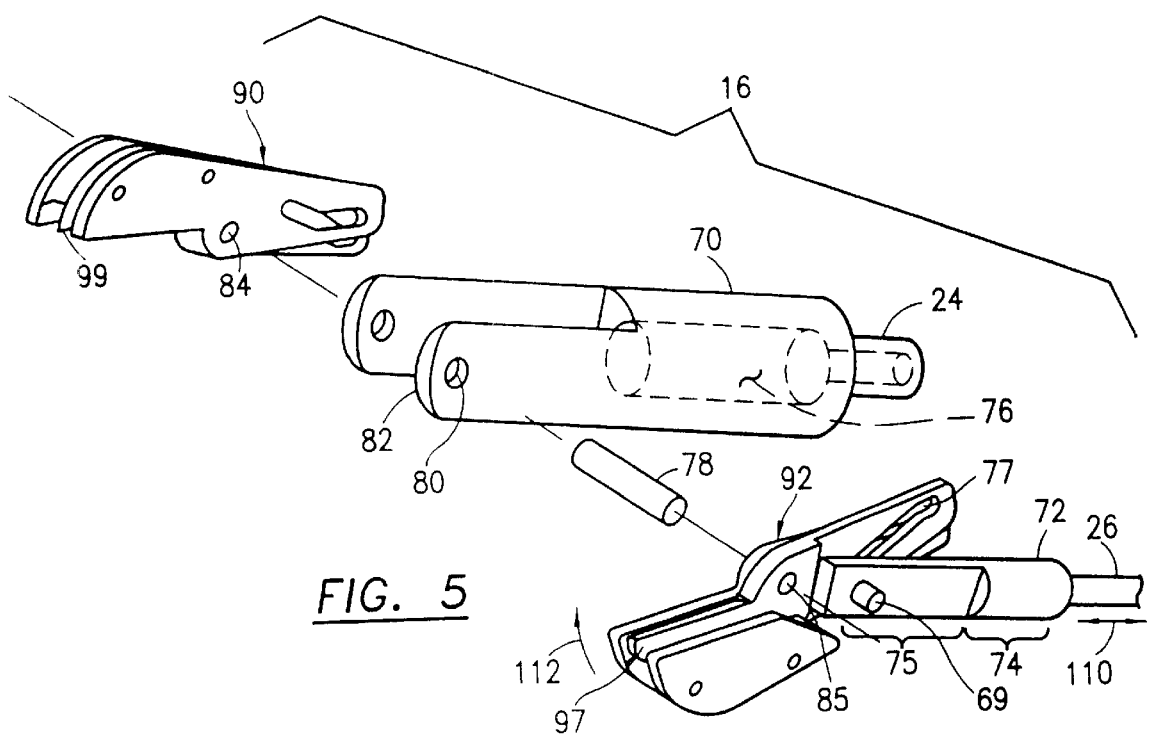
FIG. 5
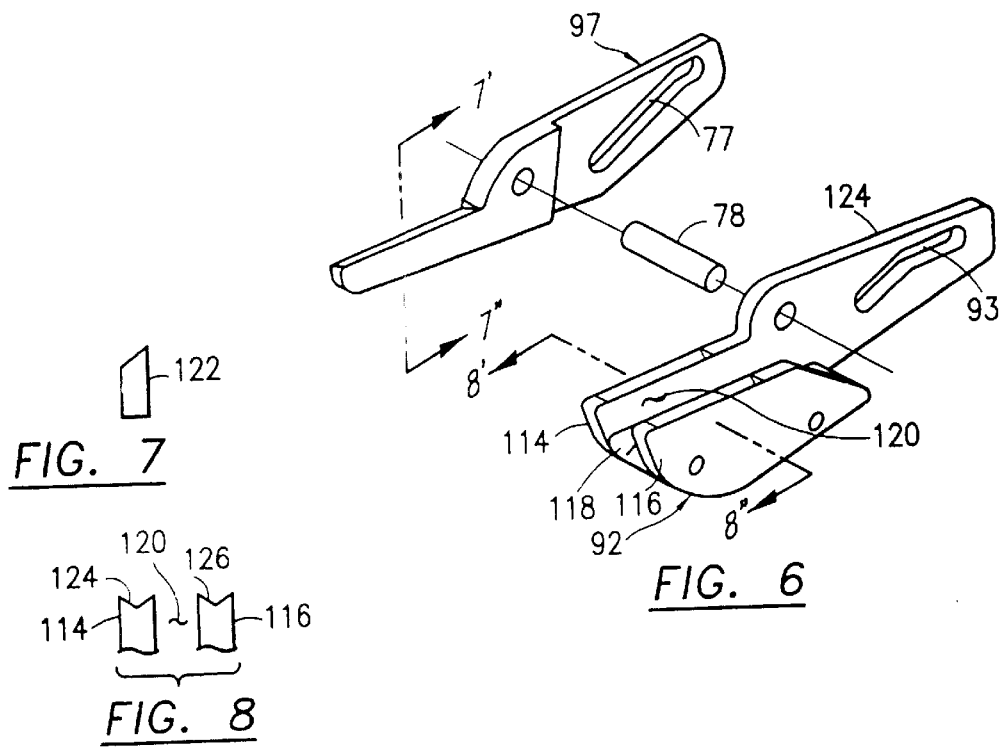
FIG. 7
FIG. 8
FIG. 6

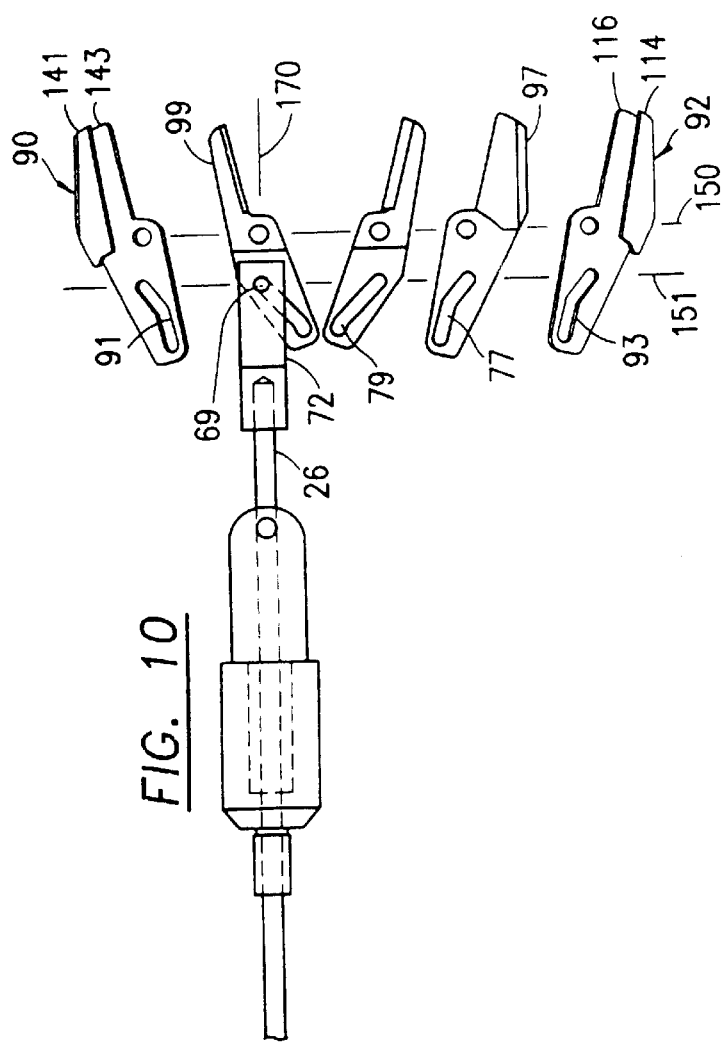
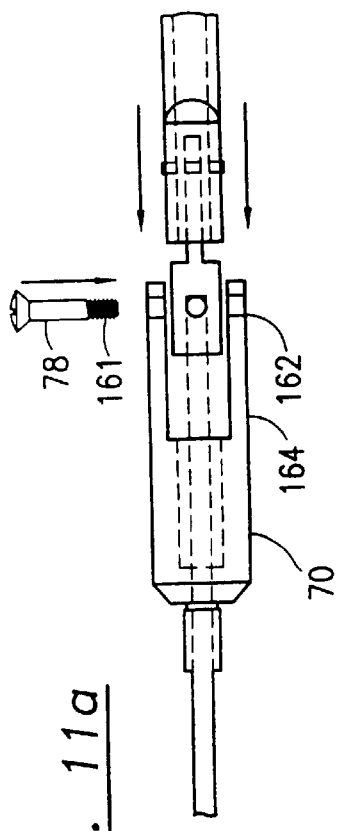
FIG. 10
FIG. 11a

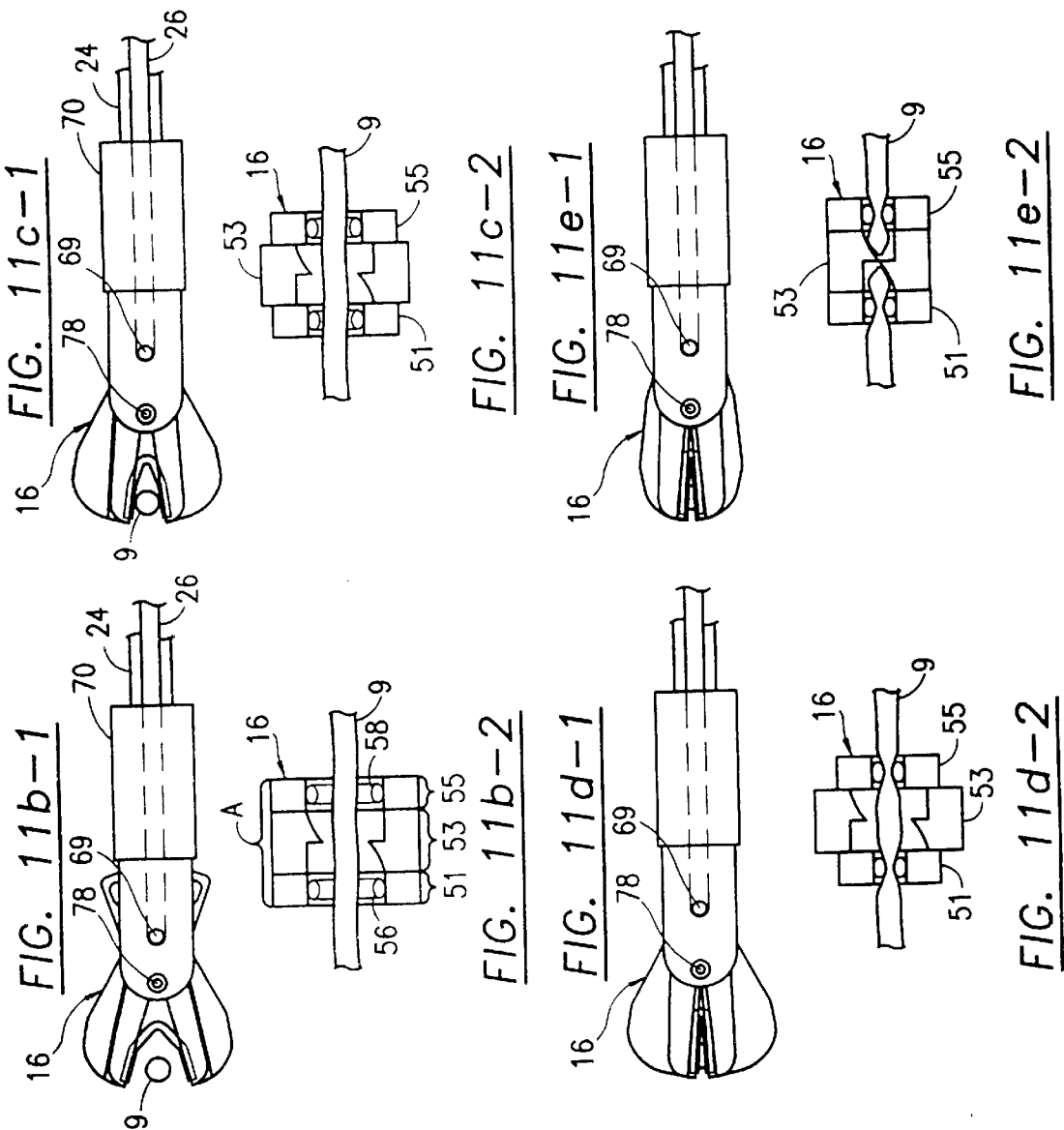

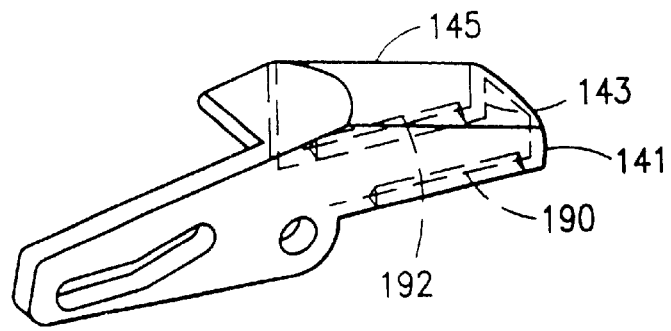
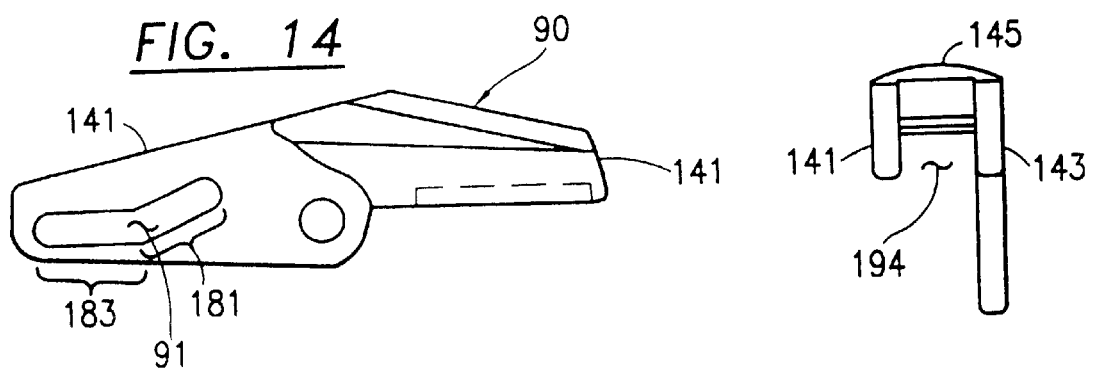
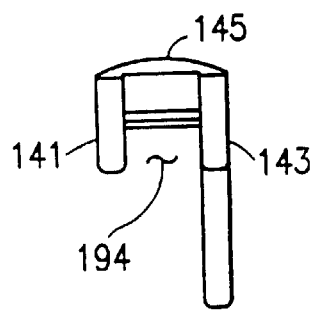
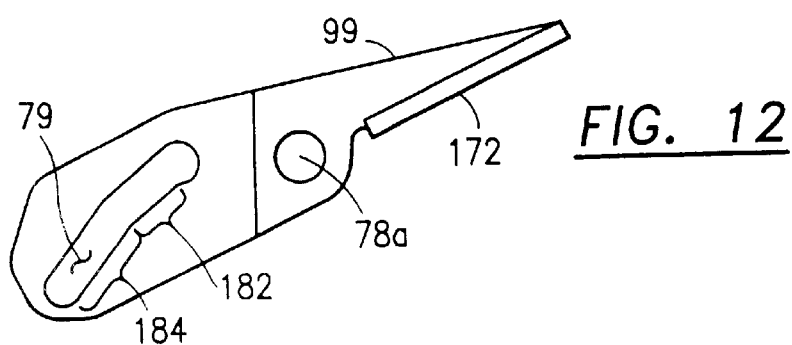
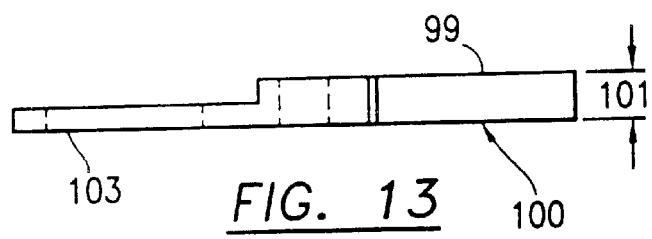

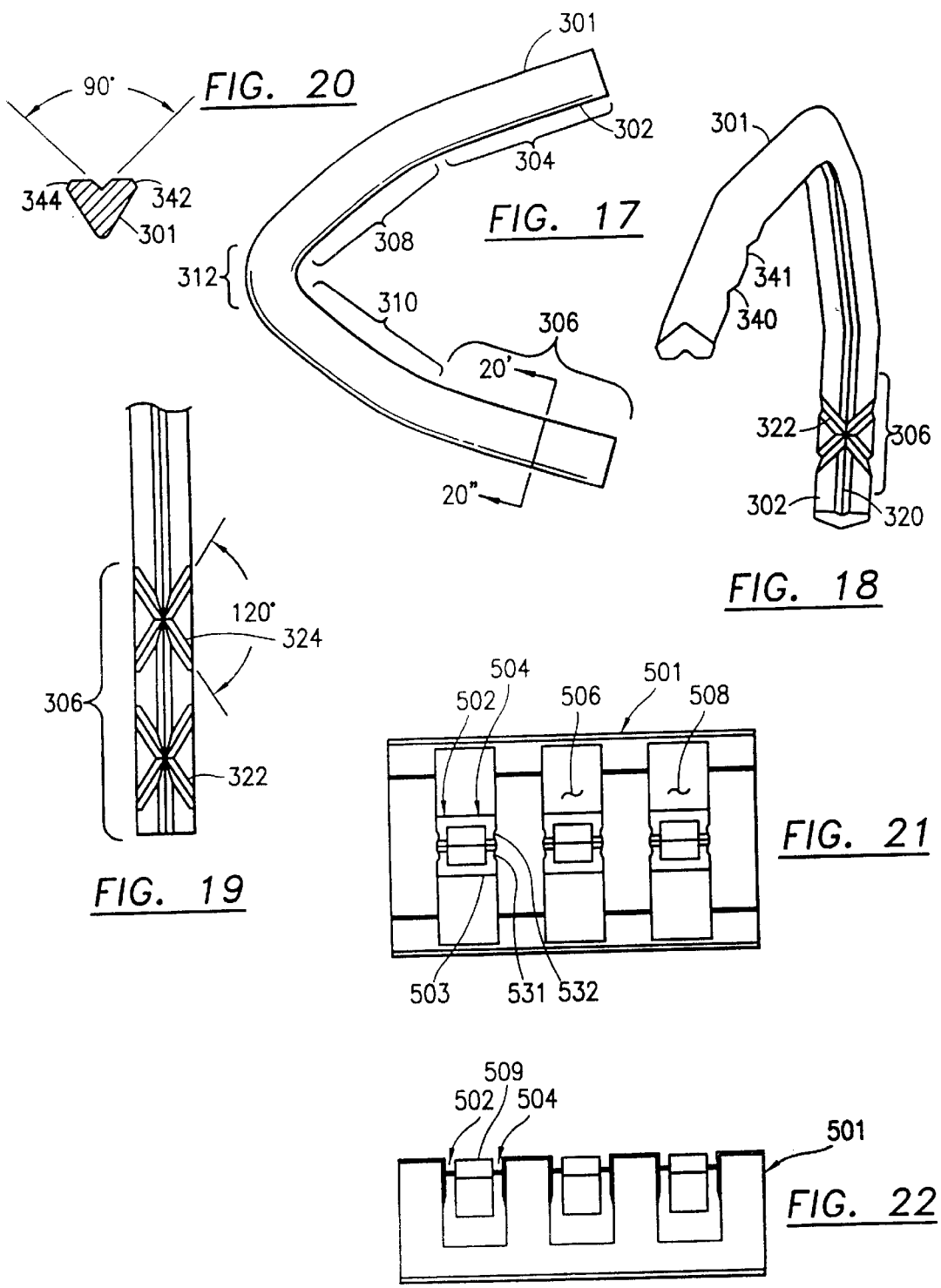

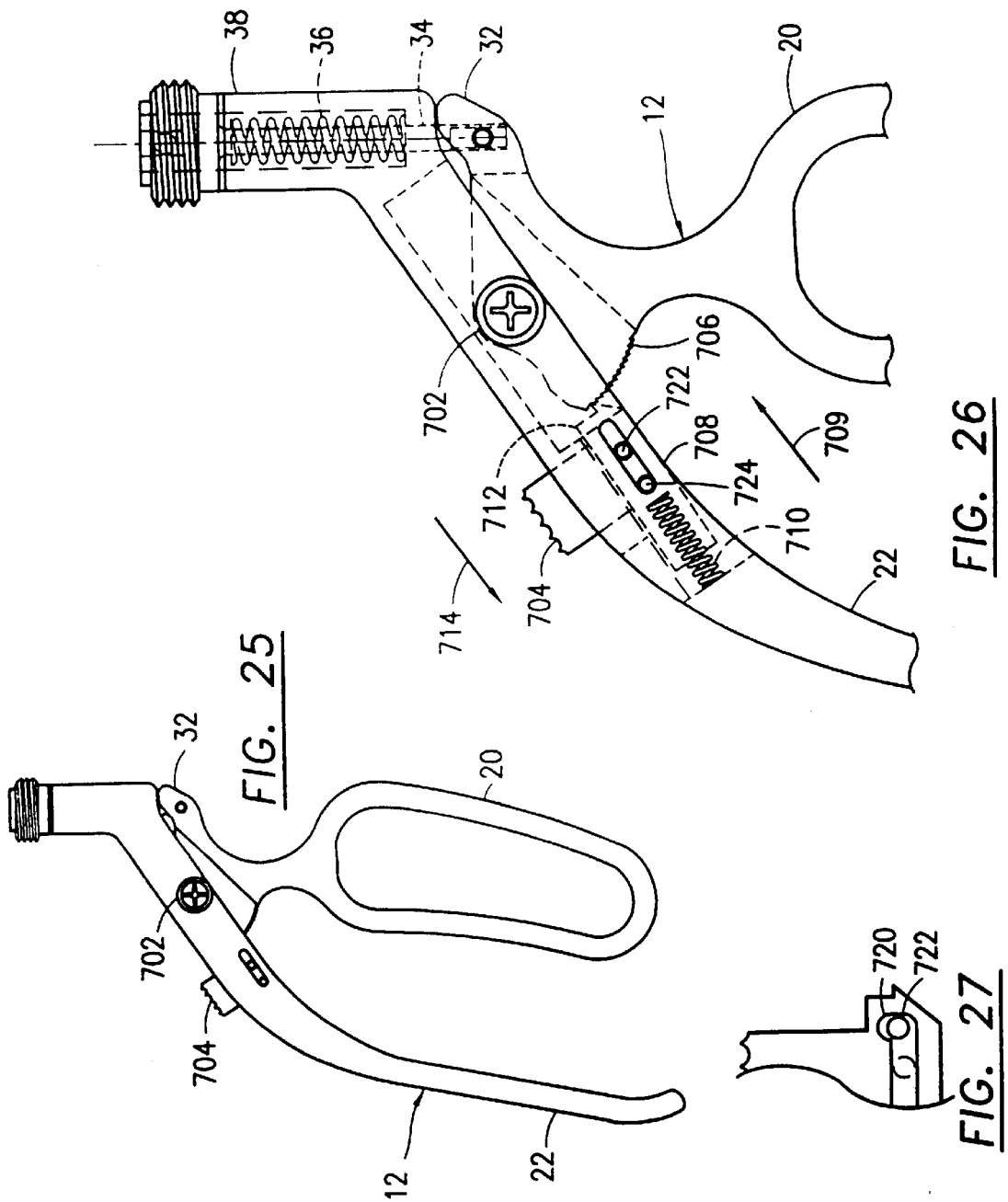

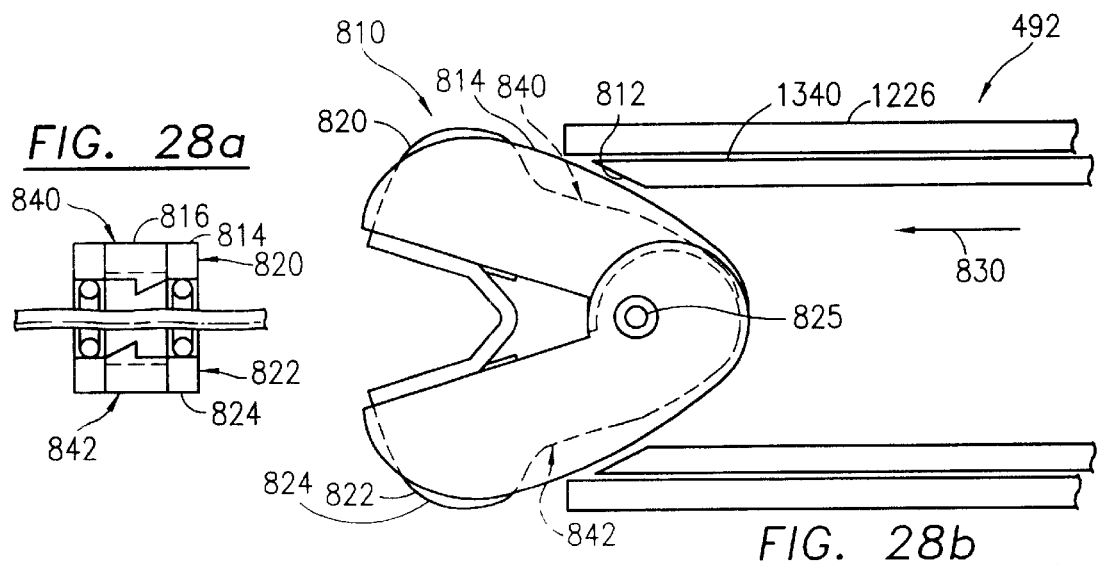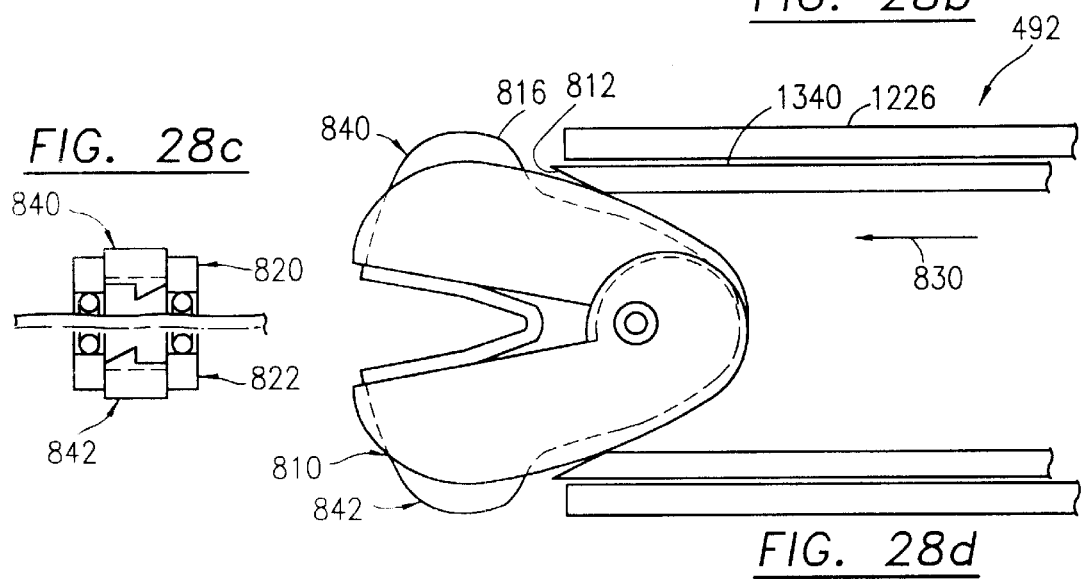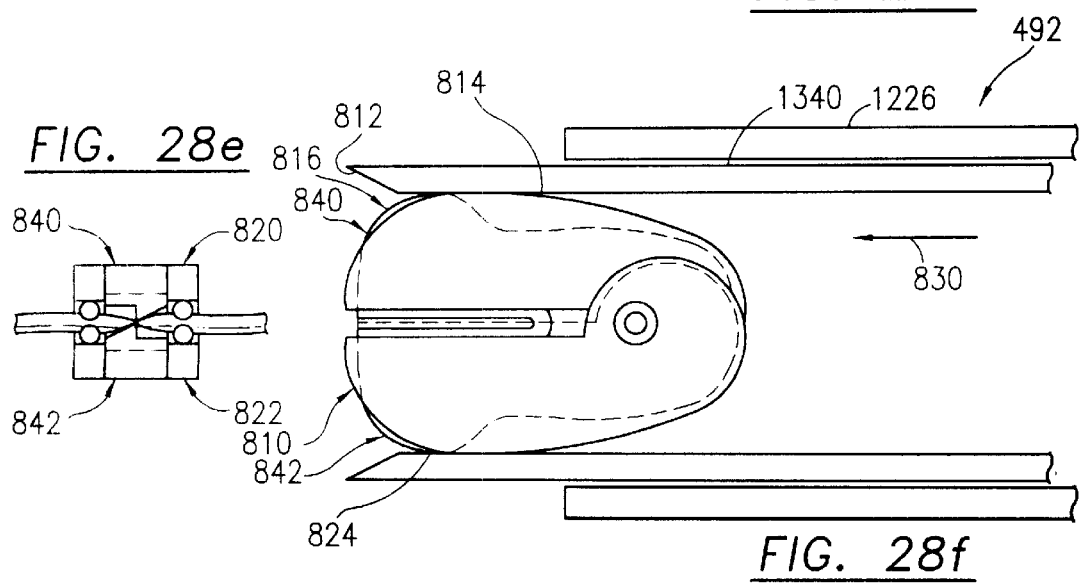

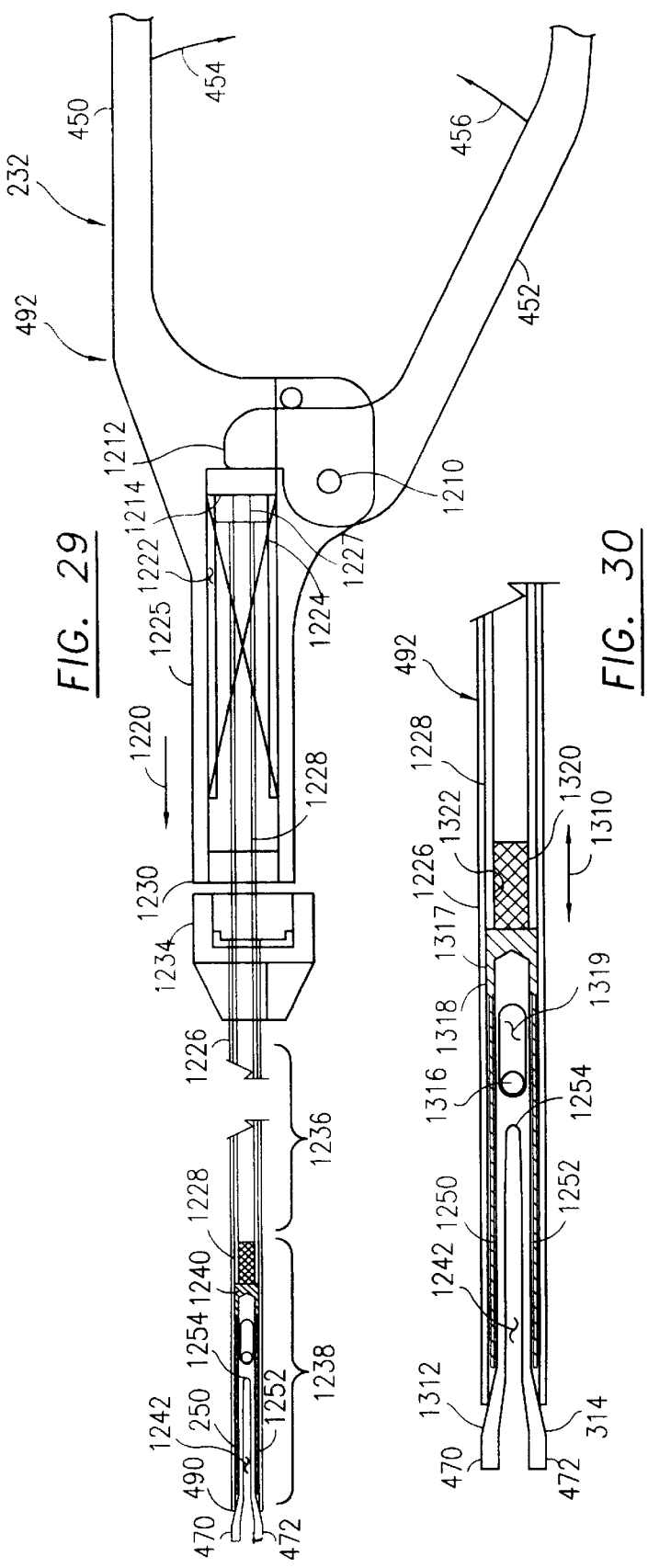

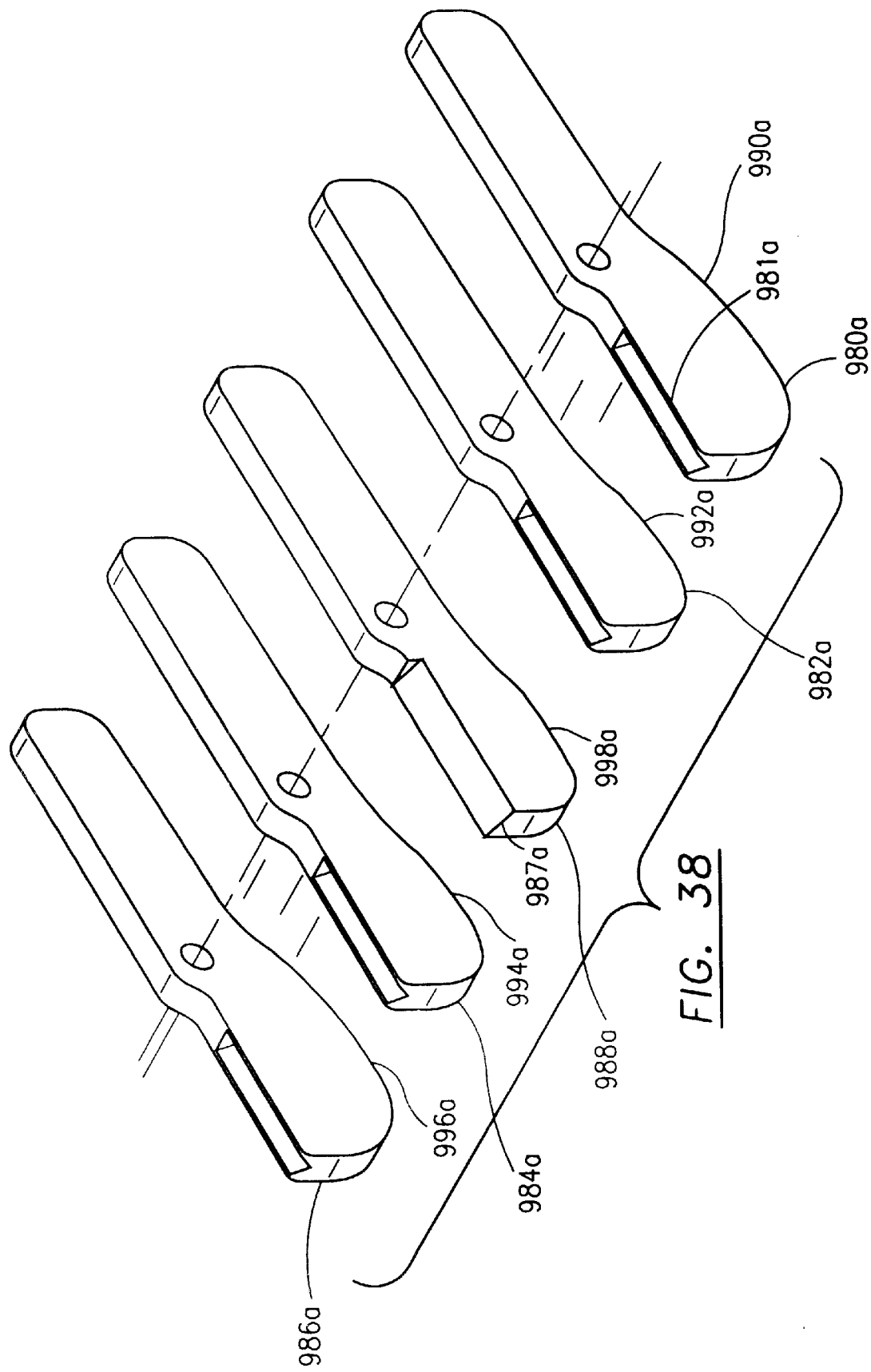

SURGICAL INSTRUMENT FOR APPLYING MULTIPLE STAPLES AND CUTTING BLOOD VESSELS AND ORGANIC STRUCTURES AND METHOD THEREFOR

This is a continuation-in-part of U.S. patent application Ser. No. 09/235,412 filed Jan. 22, 1999, now pending.

The present invention relates to a surgical instrument for stapling, with at least two, and possibly more, surgical clips and then subsequently cutting a blood vessel or other organic structure and a method for stapling and cutting.

BACKGROUND OF THE INVENTION

The following patent references show surgical instruments having various features. U.S. Pat. No. 3,675,688 to Bryan describes a surgical tool for ligating, suturing and dividing organic tubular structures in a single unitary operator movement by first capturing the tubular structure in a jaw subassembly which encompasses both the forward exposed side of the tubular structure and the opposing, rearward side of the tubular structure (FIG. 11a, jaw size beta). Thereafter in a single operator stroke, a rod moves rearward with respect to the distal end of the instrument, ligating the organic structure, then firing a pair of staples over the structure (ejecting the staples with a spring force) and cutting the tubular structure with a knife intermediate the staples.

U.S. Pat. No. 3,777,538 to Weatherly discloses a surgical device which applies a singular clip to ligate an organic tubular structure.

U.S. Pat. No. 4,602,629 to Schnirman discloses a combined surgical blade and clip assembly including a pair of opposing platforms, joined together by a spring hinge. The platforms have multiple platform levels. The lowest levels hold clips which, upon depression of the hinge and compression of the low level platform surfaces together, clips legs closed about the tubular organic structure. Thereafter upon further compression of the hinge and opposing platforms, the pair of opposing high level platform surfaces move towards each other. A blade is mounted on at least one high level platform. Upon compression of the high level platforms, the blade cuts the tubular structure. The opposing high level platform has an anvil or a blade sheath to guide the blade. The blade and clip assembly is carried in the jaws of a surgical clamp. The clips, carried on the lower platform levels, are dispensed on the tubular structure and remain thereon after the tube is cut. U.S. Pat. No. 5,104,394 to Knoepfler discloses an automatic stapler which staples or clips and then cuts an organic tubular structure. Upon compression of the operator's handle, jaws carrying a staple clip close at the distal end of the device. If the operator wants to cut an item at the stapled site, he or she moves a thumb slide, located at a remote location on the handle, away from the compressible hand grip. The system dispenses a single staple clip during each operation. U.S. Pat. No. 5,336,229 to Noda discloses a dual stapler or ligating assembly with a surgical blade. In operation, the operator depresses a compressible handle and then depresses a separate trigger to transect the organic tissue. U.S. Pat. No. 5,447,513 to Davison discloses a stapler and surgical blade assembly having a single stapler jaw pair, a blade and blade guide subassembly, angularly displaced with respect to each other at the distal end of the stapler-blade assembly. See FIG. 3. To staple and cut the blood vessel, the operator staples one location on the vessel, moves the distal end of the instrument along the vessel to a second location, dispenses another staple and then maneuvers the blade slide, on the instrument's handle, and cuts the vessel at an intermediate position.

U.S. Pat. No. 3,631,707 to Miller discloses a hemostatic clamp carrying a surgical staple or clip for blood vessels.

The following patent reference shows a surgical handle design: U.S. Pat. No. 5,171,250 to Yoon discloses a handle which the operator must compress to close and dispense a staple clip on an anatomical structure. Prior to compressing the handle, the operator squeezes a trigger then rotates a pivoting lock bar away from the compressible handle. After dispensing the staple, the operator depresses a second compressible handle located at a proximal end above the primary compressible handle.

The following patent references show various clip grip patterns for surgical staples or clips: U.S. Pat. No. 5,192,288 to Thompson discloses in FIG. 11aB a surgical clip with a shallow, longitudinal grove (having a truncated, conical cross-section) and V-shaped cross channels. The vertex of the V channels is directed towards the vertex of the staple clip. U.S. Pat. No. 5,269,792 to Kovac discloses surgical clips in FIGS. 13A, B and C with a longitudinal channel (having a pentagonal, cross-sectional shape) and laterally disposed V channels (also pentagonal). The V channels have vertices directed away from the primary vertex of the staple clip.

U.S. Pat. No. 3,326,216 to Wood shows a large, central channel and cross or lateral channels having an equal depth. U.S. Pat. No. 3,867,944 to Samuels shows longitudinally disposed, peripherally located, protrusions. U.S. Pat. No. 4,188,953 to Klieman shows a clip with flat surface and diagonal channels. U.S. Pat. No. 4,449,530 to Bendel shows a clip with a cross-hatch active surface. U.S. Pat. No. 4,696,396 to Samuels shows clips with centrally aligned protrusions. U.S. Pat. No. 4,844,066 to Stein shows clips with a central, longitudinal channel and lateral cross channels. The longitudinal channel is generally rectilinear. Stein's clip first deforms the fore-ends of clip legs, then closes about tubular organic structure. U.S. Pat. No. 4,971,198 to Mericle shows, in FIG. 6, a clip with a shallow, longitudinal channel and deep cross or lateral channels. The lateral channels are square and deep.

The following patent references show various surgical clips or staple holders: U.S. Pat. No. 3,713,533 to Reimels; U.S. Pat. No. 4,076,120 to Carroll; and U.S. Pat. No. 4,146,130 to Samuels.

OBJECTS OF THE INVENTION

It is an object of the present invention to provide a surgical instrument for stapling and cutting a blood vessel or other organic structure in a singular, operative stroke. As used herein the term "blood vessel" refers to any anatomical, tubular structure in a mammal. The term "organic structure" refers to any anatomical structure in a human or other mammal. Sometimes the term "blood vessel" is used as a shorthand reference to both "blood vessels" and "organic structures."

It is another object of the present invention to provide a method for surgically stapling and cutting a blood vessel or other organic structure in a body by simultaneously clipping both sides of a segment of a blood vessel (or other organic structure) and then, in the same, singular, operative stroke, cutting the segment wherein the clipping occurs during an initial portion of the stroke and the cutting occurs during a subsequent portion of the stroke.

It is an additional object of the present invention to provide surgical clips having unique, non-slip, high traction pattern to clamp or clip a blood vessel or other organic structure in the body.

It is an additional object of the present invention to provide a surgical instrument wherein a pair of surgical staple clips are first clamped onto the blood vessel or other organic structure in the body and then, during the single, operative stroke, the blood vessel or organic structure is cut.

It is an another object of the present invention to provide a surgical instrument with clip jaw sets and a scissor jaw set which are actuated at different times based on a single stroke of a cam moving in dissimilar cam follower channels.

It is an additional object of the present invention to provide a surgical instrument wherein a cam pin is retracted and the clip jaw sets first close on the blood vessel and, immediately thereafter, the scissor jaw set cuts the blood vessel or organic structure based upon further retraction of the cam pin. The cam pin moves in the clip-action cam follower channel and the cut-action cam follower channel.

It is an additional object of the present invention to provide a surgical instrument with a compressible handle that retracts a rod carrying the cam pin at the distal end of the rod.

It is another object of the present invention to pivotally mount the clip jaw sets and the scissor jaw set on a common lateral axis at the distal end of an elongated tube within which longitudinally moves an actuator rod.

It is another object of the present invention to provide a method for surgically stapling and cutting a segment of a blood vessel or other organic structure utilizing a retracting rod to simultaneously clip both sides of the blood vessel segment (or other organic structure segment) and then cut the segment during a singular, operative stroke and rod retraction.

It is a further object of the present invention to provide a method utilizing two U-shaped surgical staple clips and simultaneously collapsing both U-shaped clips onto the blood vessel or organic structure segment.

It is another object of the present invention to provide a method wherein the clipping and cutting steps include the step of translating the singular rod retraction into sequential pivotal movement about a common axis at the distal end of the surgical instrument.

It is another object of the present invention to provide a handle for a surgical instrument.

It is a further object of the present invention to provide a handle with a movable handle member having a tactile response surface which abuts a response wall on a stationary handle member.

It is a further object of the present invention to provide the tactical response surface which informs the operator, via tactile sensations, that he or she has moved the handle and has retracted or extended the rod through certain discrete segments thereby signaling to operator that the surgical instrument has clipped and, subsequently, cut the blood vessel or organic structure.

It is another object of the present invention to provide various tactile response surfaces on the movable handle member and different tactile response walls on the stationary handle member.

It is an additional object of the present invention to provide a latch or a ratchet lock on the handle.

It is another object of the present invention to provide a surgical staple clip for use with the surgical instrument.

It is a further object of the present invention to provide a surgical staple clip having a longitudinal center channel on a clip face and X-shaped channels with vertices coextensive with the longitudinal center channel to provide a high degree of traction on the clip face.

It is an additional object of the present invention to provide a surgical staple clip wherein two X-shaped channels are defined on terminal planer facial segments of the clip face.

It is another object of the present invention to provide a surgical appliance capable of clipping a plurality of surgical clips onto a blood vessel or organic structure.

It is another object of the present invention to provide a surgical appliance wherein the clip carrying jaw members and the scissor jaw members are closed based upon cam follower surfaces.

It is a further object of the present invention to provide cam actuated jaws and scissors which are closed at different rates and/or at different times based upon different shapes for the cam follower channels or cam follower surfaces.

It is another object of the present invention to provide a surgical appliance capable of clipping a plurality of surgical clips onto a blood vessel or organic structure.

SUMMARY OF THE INVENTION

The surgical instrument for stapling and cutting a blood vessel or other organic structure utilizes at least two, and possibly more, surgical staple clips. The surgical instrument in one embodiment includes an elongated tube with a longitudinally movable rod disposed therein. A handle, mounted on a proximal end of the tube, includes a movable member which causes the movable rod to move longitudinally. In one embodiment, a pair of surgical staple clip carrying jaw sets are pivotally mounted on a common lateral axis located at the distal end of the elongated tube, each clip jaw set includes at least two jaw members, and each jaw member defines a clip action cam following channel. In another embodiment, outboard edges of each jaw member define cam following surfaces. In a further embodiment, jaw members are ganged together and move as a unit based upon a cam follower surface motivated by a cam actuator member. The surgical appliance and clip jaws can be configured to attach two, three, four, five, six or more surgical clips onto the blood vessel or organic structure prior to cutting the vessel or structure. In a different embodiment with more than eight clip carrying jaws (four surgical clips), the cam follower channels or cam follower surfaces have substantially different shapes such that different clips close on the blood vessel or organic structure at different rates and at different times with respect to the longitudinal position of the movable rod. A method of simultaneously clipping at least two, and possibly more, surgical clips and then cutting the blood vessel or other organic structure is also disclosed herein.

BRIEF DESCRIPTION OF THE DRAWINGS

Further objects and advantages of the present invention can be found in the detailed description of the preferred embodiments when taken in conjunction with the accompanying drawings in which:

FIG. 1 diagrammatically illustrates a side-elevational view of the surgical instrument;

FIG. 2 diagrammatically illustrates a top view of the surgical instrument;

FIG. 3 diagrammatically illustrates a cross-section of the surgical instrument from the perspective of section line 3'–3" in FIG. 1;

FIG. 5 diagrammatically illustrates an exploded view of the end piece showing one clip jaw set and an upper scissor jaw member, the common lateral axis, the distal end of the elongated tube, the other clip jaw set and lower scissor jaw member and the distal end of the movable rod;

FIG. 6 diagrammatically illustrates an exploded view of one clip jaw set and the lower scissor jaw member;

FIGS. 7 and 8 diagrammatically illustrate cross-sectional views of the blade of the scissor jaw member and the clip carrying channels of the clip jaw members from the perspective of section lines 7'–7" and 8'–8" in FIG. 6;

FIG. 10 diagrammatically illustrates an exploded view of the pair of clip jaw sets, the scissor jaw set, the movable rod and the distal end of the elongated tube;

FIG. 11a diagrammatically illustrates a top view of an exploded, partially assembled surgical instrument and the common axis pin for the end piece;

FIGS. 11b through 11e diagrammatically illustrate the method which clips segment A of a blood vessel and then cuts the blood vessel or other organic structure;

FIGS. 12 and 13 diagrammatically illustrate a side view and a top view of the scissor jaw member, respectively;

FIGS. 14, 15 and 16 diagrammatically illustrate a side view, an end view and perspective view of a clip jaw member, respectively;

FIG. 17 diagrammatically illustrates a side view of a surgical clip;

FIG. 18 diagrammatically illustrates a perspective view of the surgical clip showing the X-shaped channel on the terminal, planar facial segment and the longitudinal center channel;

FIG. 19 diagrammatically illustrates the surgical clip with two X-shaped channels on the terminal planar facial segment;

FIG. 20 diagrammatically illustrates a cross-section of the clip from the perspective of section line 20'–20" in FIG. 17;

FIGS. 21 and 22 diagrammatically illustrate a top view and a side view of the surgical staple clip holder;

FIG. 25 diagrammatically illustrates a side view of the handle for the surgical instrument with a latch or a ratchet mechanism and the protruding operator control surface;

FIG. 26 diagrammatically illustrates a detailed view of the responsive tactile piece, the biased member, fine-tooth ridges on the tactile response surface and the operator control surface; and, FIG. 27 diagrammatically illustrates the latch for the biased member with a detent and complementary nub to latch the biased member away from the tactile response surface on the movable handle member.

FIGS. 28a through 28f diagrammatically illustrate exterior cam surfaces on clip jaws and scissor jaws which are closeably actuated by the longitudinal extension of a rod, tube or extending member.

FIGS. 29, 30, and 31 diagrammatically illustrate another surgical appliance for utilizing a plurality of surgical clips (with a scissor jaw set (not shown)), a detailed end view showing an "open jaw" position for the surgical appliance, and a substantially closed jaw configuration.

FIG. 38 diagrammatically illustrates lower clip carrying jaw members and lower scissor jaw member which members cooperate with the upper clip jaws and scissor illustrated in FIG. 37.

DETAILED DESCRIPTION OF THE PREFERRED EMBODIMENTS

Figure 4:
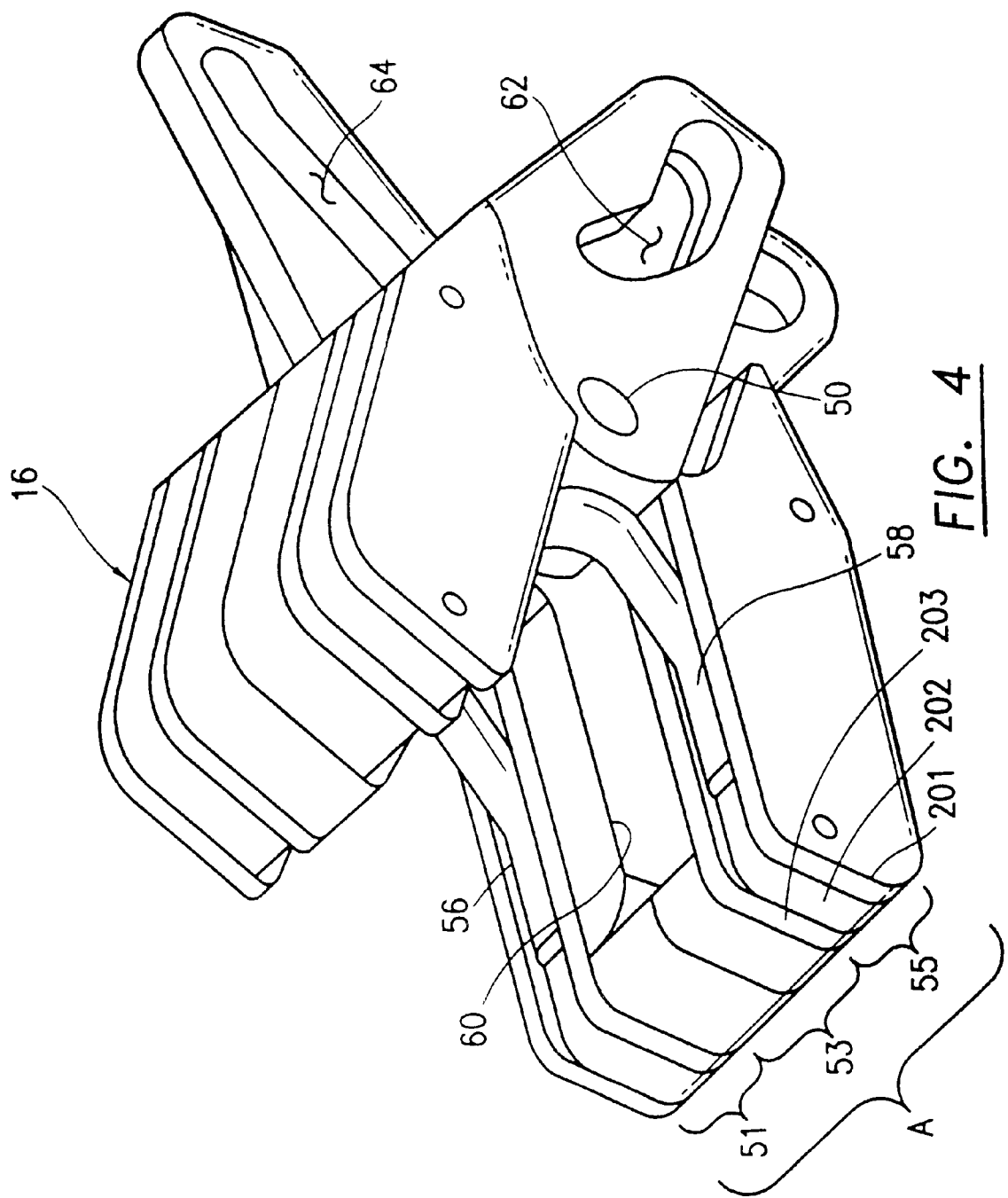
FIG. 4 diagrammatically illustrates a perspective view of the end piece for the surgical instrument showing the clip jaw sets and the scissor jaw set.

The present invention relates to a surgical instrument for stapling and cutting a blood vessel or other organic structure in a body, a method for surgically stapling and cutting, a handle for a surgical instrument and a surgical staple clip.

FIGS. 1–16 generally diagrammatically illustrate preferred embodiments of the surgical instrument. FIGS. 17–20 generally diagrammatically illustrate the surgical clip. FIGS. 21 and 22 generally diagrammatically illustrate the clip holder. FIGS. 23–27 diagrammatically illustrate several handle configurations for the previously discussed surgical instrument or other surgical instruments wherein an axially movable rod actuates a surgical mechanism at a distal end of the instrument.

FIG. 1 generally diagrammatically illustrates surgical instrument 10 having a handle 12 at its proximal end 14 and an end piece 16 at its distal end 18. End piece 16 is the surgical mechanism operated by the handle in the embodiment shown in FIGS. 1 and 2. FIG. 2 diagrammatically illustrates a top view and particularly shows movable handle member 20 disposed generally above stationary handle member 22. Surgical instrument 10 includes an elongated tube 24 and a movable rod 26 disposed within tube 24. FIG. 3 diagrammatically illustrates a cross-sectional view of instrument 10 and particularly rod 26 disposed within elongated tube 24. In a working embodiment, tube 24 closely encapsulates rod 26.

With respect to handle 12, movable handle member 20 is pivotally attached at pivot point 28 to stationary handle member 22. Movable handle member 20 moves in the direction shown by arrow 30 when the operator compresses the handle. Stem 32, at a point beyond pivot 28, is attached to actuator rod 34. Handle 20 is biased to an outboard position (shown in FIG. 1) by spring 36. Further details of handle 12 are shown and discussed later in conjunction with FIGS. 23–27. Only certain operational items are discussed with respect to FIG. 1.

The inboard portion of handle 12 terminates in a male threaded joint 38. Actuator rod 34 terminates in a female coupler (not shown in FIG. 1) which mates with male coupler piece 40 at the proximal end of movable rod 26. This mechanical coupling system is shown in detail later in connection with FIG. 24. It should be noted that the male and female couplers may be transposed such that movable rod 26 terminates in a female coupler. A female coupling unit 42 (illustrated in FIG. 1) slides over rod 26 as shown by double headed arrow 44. Also, as discussed later in connection with FIG. 24, female coupler unit 42 has female threads and a freely rotatable outer unit such that when female coupler is rotated as shown by double headed arrow 46, the elongated tube 24 rotates thereby rotating end piece 16.

FIG. 4 is a diagrammatic, perspective view of end piece 16. As described in detail hereinafter, end piece 16 includes a plurality of pivoting members, all of which pivot about a common lateral axis 50. One of these members is a clip jaw member generally designated at lateral jaw area 51, a scissor jaw member, generally designated at lateral jaw area 53 and another clip jaw member generally designated at lateral jaw area 55. The clip jaw sets carry surgical clips 56 and 58. The scissor jaw set carries scissor blades, one of which is scissor blade 60 in the lower portion of the jaw mouth. As described in detail hereinafter, the clip jaw sets initially close based on the two-part, linear configuration of clip-action cam follower channels, one of which is cam follower channel 62. Thereafter, the scissor jaw set closes based upon the two-part, linear configuration of the cut-action cam follower channel generally designated as channel 64.

FIG. 5 diagrammatically illustrates an exploded view of end piece 16. The elements in FIG. 5 are not shown in sequential assembly order. Elongated tube 24 terminates in end member 70. Movable rod 26 terminates in rod end piece 72. Rod end piece 72, and particularly inboard segment 74 (inboard or close to rod 26), moves longitudinally in cavity 76 of end member 70. The two clip jaw sets and scissor jaw set pivot about a common lateral axis established by pin or bolt 78. Pin 78 passes through holes or apertures, one of which is aperture 80 at the outboard end 82 of end member 70. Pin 78 also passes through hole or aperture 84 and jaw member 90. Pin 78 also passes through an aperture in jaw set 92. Further, pin 78 passes through aperture or hole 85 in scissor jaw member 97.

A laterally extending cam 69 extends laterally from an outboard region 75 of rod end member 72. The term "laterally" refers to a position or direction generally normal (perpendicular) to rod 26 and tube 24. As explained later in great detail, since the jaw sets 90, 92 and the scissor jaw members 97, 99 all pivot about a common lateral axis (defined by pin 78), when rod 26 moves longitudinally (as shown by double headed arrow 110), cam 69 moves in the cam follower channels established at the inboard plate segments of the jaw sets 90, 92 and scissor jaw members 97, 99. For example, scissor jaw member 97 includes a cut-action cam follower channel 77. When cam 69 moves in the direction shown by arrow 10 (to the right in FIG. 5), a retracting motion), jaw member 97 moves upward as shown by arrow 112 due to cam 69 moving to the right and in cut-action cam follower channel 77. This is described in greater detail in later figures.

FIG. 6 diagrammatically illustrates scissor jaw member 97, pin 78 establishing the common lateral axis and clip jaw set 92. Clip jaw set 92 includes a first and a second jaw member 114, 116, joined together by a base plate 118. A space 120 is defined between jaw members 114, 116. A cutting blade 122 for scissor jaw member 97 is disposed in space 120.

Jaw set 92, in the illustrated embodiment, defines the lower jaw mouth for end piece 16. Jaw member 114 is a plate which includes or defines a backplate 124. Back plate 124 is inboard with respect to pin 78 defining the common axis and is also inboard with respect to the jaw mouth fore end piece 16. The inboard backplate 124 defines a clip-action cam follower channel 93. Cam 69 is disposed in cam follower channel 93. As used throughout this specification, the term "clip" refers to a surgical staple clip rather than an action which "cuts." Hence, "clip-action" refers to collapsing a surgical staple clip onto a blood vessel or other organic structure in a body.

Scissor jaw member 97 includes a backplate with a cut-action cam follower channel 77 within which moves cam 69.

As shown in FIG. 6, cam 69, when moving in clip-action cam follower channel 93 will close jaw plates 114, 116 at a time prior to the closure of scissor blade 122 of scissor jaw member 97. The closure of clip jaw set 92 prior to the closure of scissor jaw member 97 is due to the fact that clip-action cam follower channel 93 has a greater angular offset, offset from the instrument's axial center line, as compared with the angular offset for cut-action cam follower channel 77. The comparatively greater angular offset of the clip-action follower channel in the first or initial linear channel segment causes the clips to close before the scissor jaws close.

FIG. 7 diagrammatically illustrates a cross-section of the blade on the scissor jaw member blade portion 122. FIG. 7 is viewed from the perspective of section line 7'-7" in FIG. 6.

FIG. 8 diagrammatically illustrates the cross-sectional view of clip retention channels 124, 126 on jaw set members or plates 114, 116. Other clip retaining channels may be provided on clip plates 114, 116. As stated earlier, scissor blade 122 moves within space 120 intermediate jaw plates 114, 116. Accordingly, baseplate 118 (connecting jaw plates 114, 116) protects the radial backside of the scissor blades. This base plate 118 may prevent fouling of the blades during the surgical procedure.

Figure 9:
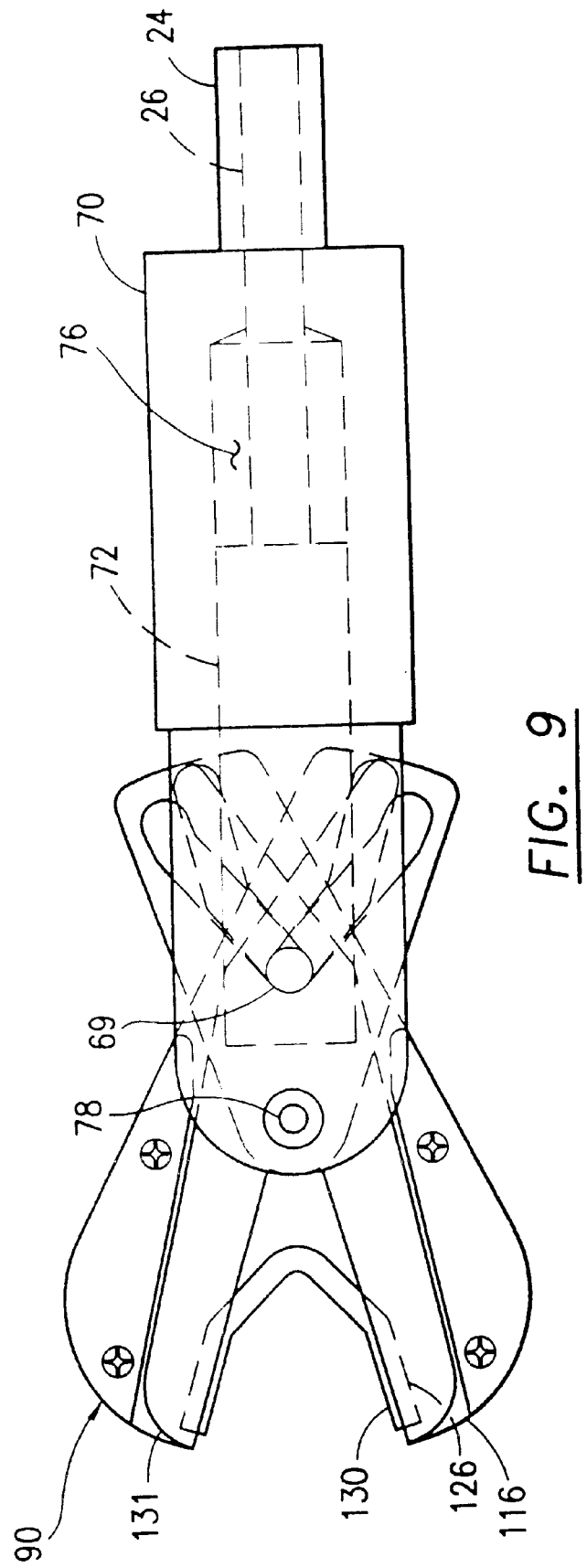
FIG. 9 diagrammatically illustrates the end piece and various cam follower channels, the distal end of the elongated tube and the distal end of the movable rod.

FIG. 9 diagrammatically illustrates movable rod 26 closely captured and retained in elongated tube 24. Rod end member 72 is shown movably disposed within space 76 of tube end member 70. The clip jaw sets and scissor jaw set pivot about pin 78. Cam 69 moves within the aforementioned cam follower channels. Jaw plate 116 retains clip 130 in clip channel 126. The generally U-shaped clip 130 has a leg which is captured by jaw plate 131 of clip jaw set 90. The cam follower channels are also illustrated in FIG. 9.

In FIG. 9, the clip-action and cut-action cam follower channels have the same initial or leading angular offset (with respect to the axial center line of rod 26); however, the length of the cut-action initial or leading channel segment is longer than the initial channel segments of the clip-action cam follower channels. In this manner, the clips are collapsed or "clipped-on" the blood vessel and then the scissor blades are forced to close further (e.g., causing on lower blade edge 122 (FIG. 6) to bypass the upper blade edge) to ensure that the blood vessel or other organic structure of the surgical site is cut or completely severed. As used herein, reference to "a blood vessel" also includes the concept of clipping and cutting an organic structure at a surgical site in a mammal.

FIG. 10 diagrammatically illustrates an exploded view of the surgical end piece and shows the two clip jaw sets 90, 92 and the scissor jaw set which includes scissor jaw members 97, 99. Lower clip jaw set 92 includes jaw plates 114, 116 (see FIG. 6). Clip jaw set 90 includes jaw plates 141, 143. A single surgical clip (not shown) resides in the clip channels of jaw plates 114, 141. This is generally shown as lateral jaw region 55 in FIG. 4 which shows a perspective view of end piece 16. The clip channels for jaw plates 116, 143 retain clip 56 as shown in lateral jaw area 51 of FIG. 4. Scissor jaw members 97, 99 together form a scissor jaw set. The clip jaw sets 90, 92 and the scissor jaw set, collectively a single set formed by members 97, 99, all pivot about a common lateral axis illustrated as axis 150 in FIG. 10. Cam 69, which extends laterally from rod end piece 72, extends into cam follower channels 93, 77, 79, 91. All the cam follower channels define non-linear, two-part channel segments in the illustrated embodiment. Although clip-action cam follower channels 93, 91 are mirror images of each other thereby coordinating the closure of jaw plates 141 and 114 (left clip), 143 and 116 (right clip), the cut-action cam follower channels 77, 79 for the scissor jaw set 97, 99 establish different cam actions compared to the clip-action channels. Accordingly, jaw sets 90, 92 first close and then, at a subsequent time, scissor jaw members 97, 99 close.

FIG. 11a diagrammatically illustrates pivot pin 78 having a male threaded portion 161 which threadably mounts to females threads 162 on outboard extending prong 164 of tube end member 70.

Although rod 26 is shown as closing the clip jaw sets and then closing the scissor jaw sets by retraction, the surgical instrument can be reconfigured such that the clip jaw sets close when rod 26 projects or extends (in a direction opposite retraction). In this embodiment, cam 69 would be positioned at an outboard position (rather than the illustrated inboard position) with respect to common lateral axis 150. Of course, the cam follower channels would be reconfigured to translate forward axial movement into pivotal action of the clip jaw sets and the scissor jaw set.

As shown in FIG. 10, cam 69 is initially positioned on cam initial position axis 151. If protruding movement from rod 26 is utilized, cam axis 151 would be positioned to the right of common lateral pivot axis 150 in FIG. 10. Axis 150 is coextensive with pivot pin 78. The cam following channels would be altered accordingly. The claims appended hereto are meant to cover both retraction of rod 26 as well as protruding action of rod 26.

Further, the illustrated preferred embodiments of the present invention utilize clip carrying jaw sets that have jaw plates defining both upper jaw teeth of end piece 16. Another clip jaw set carries both lower jaw teeth. It should be noted that each jaw tooth could be configured as a single, planar jaw member and each jaw plate or jaw member could have a clip-action cam follower channel therein. In this alternate embodiment (not illustrated), end piece 16 would contain four clip-action cam follower channels rather than the two clip-action cam follower channels 91, 93 illustrated in the figures. The claims appended hereto are meant to cover this alternate embodiment of the present invention.

As shown in the drawings, jaw plates 114, 116 are attached together by base plate 118. Accordingly, these two jaw members of clip jaw set 92 are laterally spaced apart (see space 120 in FIG. 6) and jaw plates 114, 116 pivot conjointly. In a like manner, clip jaw plates 141, 143 are spaced apart laterally and scissor blade 99 fits within that space. Clip jaw plates 141, 143 pivot conjointly about common lateral axis 150.

If four jaw plates are utilized (defining four clip-action cam following channels), each plate would also pivot about the common lateral axis.

Although cam 69 is shown as a pin in the illustrated embodiment, the cam need not be a pin. Cam 69 may be a bar, a triangle, or a nub that laterally protrudes from movable rod 26. Cam 69 travels within and move the respective backplates of clip jaw sets 90, 92 in scissor jaw members 97, 99 based upon the clip-action cam follower channels 91, 93 and the cut-action cam follower channels 77, 79. Jaw set 90 defines the upper jaw mouth of end piece 16. Set 92 defines the lower jaw mouth.

Although the clip-action cam follower channels 91, 93 are mirror images of each other, those clip-action cam follower channels define substantially the same non-linear cam pathways. They define the same non-linear cam pathways because the upper jaw plates close at substantially the same rate and through substantially the same arcuate distance as the lower clip jaw plates.

The invention described herein also includes the concept of curved cam follower channels. Rather than utilize a broken, two linear segment follower channels, the channels may be curved to provide clip closure at different angular speeds given certain axial rod movements or smoother transitions at the clip closing positions.

The method of the present invention is best shown in connection with FIGS. 4, 10, and 11b-1 through 11e-2. When rod 26 is retracted in a singular operative stroke, cam 69 moves in clip-action cam follower channels 91, 93 and simultaneously closes the upper and lower clip jaw sets 90, 92. This results in a clip-action in lateral jaw areas 51, 55 of FIG. 4 and the collapse and closure of surgical clips 56 and 58 about a blood vessel segment spanned by region A in FIG. 4. The segment may be a segment of blood vessel (artery or vein) or a segment of an organic structure in a body. In any event, due to the high angular offset of clip-action cam follower channels 91, 93 (this angular offset is compared to the axial center line 170 in FIG. 10), the clip jaw sets close prior to the closure of scissor jaw members 97, 99. When cam 69 (starting at initial axis 151, FIG. 10) reaches the first breakpoint in the non-linear clip-action cam follower channels 91, 93 (discussed later), the cam then activates the scissor jaw members 97, 99. The scissor jaw members then close because cut-action cam following channels 77, 79 are not linearly discontinuous (compared to the clip-action channels) at that specific intermediate longitudinal position of the cam actuator 69. Accordingly, region 53 (FIG. 4) subsequently closes after clips 56, 58 are collapsed and stapled on a blood vessel segment in region A (FIG. 4).

The method simultaneously clips both sides of segment region A of the blood vessel or other organic structure with two surgical clips 56, 58 during an initial portion of the singular operative stroke and rod retraction based on longitudinal movement of rod 26. Subsequent thereto, rod 26 continues to retract thereby closing scissor members 97, 99 due to the initial linear portion defined by cut-action cam follower channels 77, 79 (FIG. 10), as compared to the initial portion of clip-action cam follower channels 91, 93. The subsequent cutting of segment A of the blood vessel or other organic structure is conducted based upon the singular operative stroke and rod retraction of rod 26. The simultaneous collapse and staple of the U-shaped clips 56, 58 onto the blood vessel is accomplished in a single, generally uniform retraction of rod 26 caused by the operator depressing or compressing handle 12 and particularly moving movable handle member 20 towards stationary handle 22. Handle 12 is diagrammatically illustrated in FIG. 1. End piece 16 translates the singular rod retraction movement of rod 26 into sequential pivotal movements of clip jaws in region 51, 55 about a common axis 50 (see FIG. 4). Subsequent thereto, further rod retraction is converted into pivotal action of the scissor jaws and the cutting of the blood vessel.

FIGS. 11b-1 through 11e-2 diagrammatically illustrate the method in accordance with the principles of the present invention. Due to the number of components and the detail of end piece 16, only major components or jaw segments or regions 51, 53 and 55 are diagrammatically illustrated in FIGS. 11b-2, 11c-2, 11d-2 and 11e-2. The sequential method is diagrammatically illustrated by viewing side elevational view of end piece 16 in FIG. 11b-1 generally concurrently with the front elevational view of end piece 16 diagrammatically illustrated in FIG. 11b-2. The method progresses by viewing FIGS. 11b-1; 11c-1; 11d-1 and 11e-1. Front end sequential views are generally shown in FIGS. 11b-2; 11c-2; 11d-2 and 11e-2.

Blood vessel or other organic structure 9 is shown in FIGS. 11b-1 and 11b-2. End piece 16 spans segment A of blood vessel 9. It should be appreciated that blood vessel 9 is illustrated herein because it is difficult to illustrate different types of organic structure which can be first clipped and then cut by the surgical instrument described herein. In FIGS. 11b-1 and 11b-2, end piece 16 is fully open. Left jaw region 51 and right jaw region 55 is in a fully open position as is scissor jaw region 53. Clips 56, 58 are illustrated in FIG. 11b-2. Also, cam 69 is in its initial position which is close to pivot point or common axis 78 as shown in FIG. 11b-1.

In FIGS. 11c-1 and 11c-2, rod 26 has been slightly retracted, thereby changing the longitudinal position of cam 69 with respect to common lateral axis or pivot point 78. This results in the partial closure of the clip jaw sets as shown by the smaller size of the jaw mouths about jaw regions 51, 55. Scissor jaw set in region 53 has not been fully closed on blood vessel 9. Dependent upon the angular offset of the cut-action cam follower channel, scissor jaw region 53 will remain in its initial position or will begin closing at a rate slower than the clip carrying jaw sets. As shown in FIG. 11c-2, jaw regions 51, 55 are closing faster than scissor jaw region 53.

In FIGS. 11d-1 and 11d-2, the clips have been fully collapsed onto blood vessel 9 and the clip carrying jaw regions 51, 55 are diagrammatically illustrated in a closed or fully collapsed position. This greatly reduces and most likely eliminates fluid flow through the blood vessel. FIG. 11d-2 clearly illustrates that the scissor jaw region 53 remains relatively open as compared with the collapsed or fully clipped on aspect of clip carrying jaw regions 51, 55. The relative dimensions and size of various components illustrated in FIGS. 11b-1 through 11e-2 are not to scale.

In FIGS. 11e-1 and 11e-2, the scissor jaw region 53 has been fully closed, thereby cutting blood vessel 9. Cam 69 (FIG. 11e-1) is far removed from pivot point or common lateral axis 78. This is the final position of cam 69 in relation to the common lateral axis 78.

FIGS. 12 and 13 show upper scissor blade 99 with a wedge shaped blade edge 172, a hole or passageway 78a for pivot pin 78 and a cut-action cam follower channel 79. As shown in FIG. 13, the blade portion 100 of scissor jaw member 99 is wider, e.g., dimension 101, then the width of the backplate 103 which defines the cut-action cam follower channel.

FIGS. 14–16 show upper jaw set 90. Upper jaw set 90 includes jaw plate 141, jaw plate 143, baseplate 145 and backplate 147. Backplate 147 defines a clip-action cam follower channel 91. Clip-action cam follower channel 91 includes an initial linear region 181 which is activated by the cam at substantially the same time as initial linear region 182 of cut-action cam follower channel 79 in FIG. 12. However, initial linear region 182 of cut-action cam follower channel 79 defines a longer initial linear segment and a channel rather than define a smaller angular offset from the axial centerline established by the movable rod. Since the length of channel segment 182 is longer than the length of channel segment 181, and since the angular offset of channel segment 181 is greater than the angular offset of channel segment 182 (with respect to axial centerline 170 in FIG. 10), jaw set 90 closes prior to closure of scissor jaw member 99. Secondary or subsequent channel segment 183 in clip-action cam follower channel 91 simply maintains the closure of the collapsed surgical clips on the blood vessel or organic structure. Secondary linear channel segment 184 of cut-action cam follower channel 79 ensures that the scissors entirely cut through the blood vessel or organic structure.

FIG. 16 diagrammatically shows clip retention channel 190 for clip plate 141 and clip retention channel 192 for clip plate 143. Base plate or member 145 supports the clip plates. Clip jaw plates 141, 143 are spaced apart and this spacing is identified in FIG. 15 as space 194. Upper scissor plate 99 is disposed in space 194 such that the clip jaw plates 141, 143 are disposed on either side of the scissor blade.

FIG. 4 diagrammatically shows that clip jaw sets are composed of multiple plates that are attached together to form a singular unit. For example, in region 55, the lower clip jaw plate includes plate members 201, 202 and 203. These plates are mounted together by an appropriate mechanism. This mechanism may include threaded bolts or other types of attachment (i.e., rivets, weld points, adhesives). At region 53, scissor jaws are defined by two members.

FIGS. 17–20 diagrammatically illustrate the surgical clips. As shown in FIG. 17, surgical clip 301 is generally U-shaped. The clips have a clip face 302 and terminal facial segments 304, 306. Clip 301 has intermediate facial segments 308, 310. Clip 301 is bent in region 312. Facial segments 304, 306, 308 and 310 are generally planar, that is, the clip portions that interface with the blood vessel are primarily planar except for the triangular or V-shaped channels cut or formed therein. Terminal planar facial segment 306 is shown in FIG. 18. The clip face 302 includes a longitudinal center channel 320 which has a triangular or V-shaped cross-section. The triangular cross-section of center channel 320 is shown in FIG. 20. FIG. 20 is a cross-sectional view of clip 301 from the perspective of section line 20'–20" in FIG. 17. The longitudinal center channel 320 extends through all of the planar facial segments 304, 306, 308 and 310.

In FIG. 18, terminal planar facial segment 306 includes an X-shaped channel 322. The vertices of this X-shaped channel 322 are coextensive with the longitudinal center channel 320.

In FIG. 19, terminal planar facial segment 306 includes a first and a second X-shaped channel 322, 324. The legs of the X-shaped channel are angularly disposed at approximately 120°. The X-shaped channels have a triangular cross-sectional shape as shown at channel end segments 340, 341 on clip 301 shown in FIG. 18.

Clip 301 includes a chamfer 342, 344 at its outer, opposing, lateral edges.

In a preferred embodiment, the clips are constructed in three sizes, small, medium and large. The legs of the clip are not parallel but are abducted to fit a clip holder shown in FIGS. 21–22. The X-shaped channels on the terminal planar facial segments and the longitudinal center channel provide a tire grip providing high traction for the clip on the blood vessel or organic structure. The lines of this X-shaped pattern with its coextensive vertices along the longitudinal center channel provide depressions in bas relief on the active clip faces which increase the frictional grip of the clip on the blood vessel from all angles.

The following Exemplary Jaw Dimension Table and Exemplary Clip Dimension Table provide size and dimensional relationship examples for one embodiment of the present invention.

| length | 0.46 inches |
|---|---|
| width single jaw set | 0.17 |
| width jaw member | 0.1 |

| depth triangular channel | 0.004 inches |
|---|---|
| clip width | 0.03 |
| d to first vertex (from clip end) | 0.045 |
| d to second vertex | 0.120 |
| chamfer | 0.06 |
| overall width (span of U-shape) | 0.24 |
| major angle | 37° |
| length | 0.2 |

The clips are constructed of titanium or tantalum. The clips are also designed with a greater angle to the diverging leg segments defining terminal planar facial segments 304, 306, in order to fit the end piece 16 tightly.

With respect to FIGS. 21 and 22, clip holders 501 retain three pair of surgical clips. One clip is mounted in space 502 and the second clip is mounted in space 504. The next pair of clips are mounted in region 506 and the third pair of clips is mounted in region 508. Clips are disposed and spaced apart by separating bracket 509 shown in FIG. 22.

Clip holder 501 is designed and packaged to be a single sterilizable package. The interior of the package and its contents are sterilized using ethylene oxide gas or gamma radiation. The packages are dated to ensure sterility. The package is opened aseptically and clips are transferred to the sterilized clipping instrument, end piece 16, by sliding the jaws of the end piece 16 into the channel of the holder and removing two perfectly aligned clipped simultaneously.

Clip holder 101 is approximately one inch or less in length. It is made of thermoplastic material or stamped material. The holder is shaped to contain metal hemostatic or marking clips in perfect alignment for transfer to end piece 16, the crimping or clipping instrument. The size of clip tray 501 is optimum to be held between the thumb and the forefinger of the user. The shape of the core 503 and notches 531, 532 are positioned in size to hold two or more clips in perfect alignment prior to transfer to the end piece 16. The clips are held in place by small notches or nubs, two of which are illustrated as notches 531, 532 and clip space 504.

Figure 23:
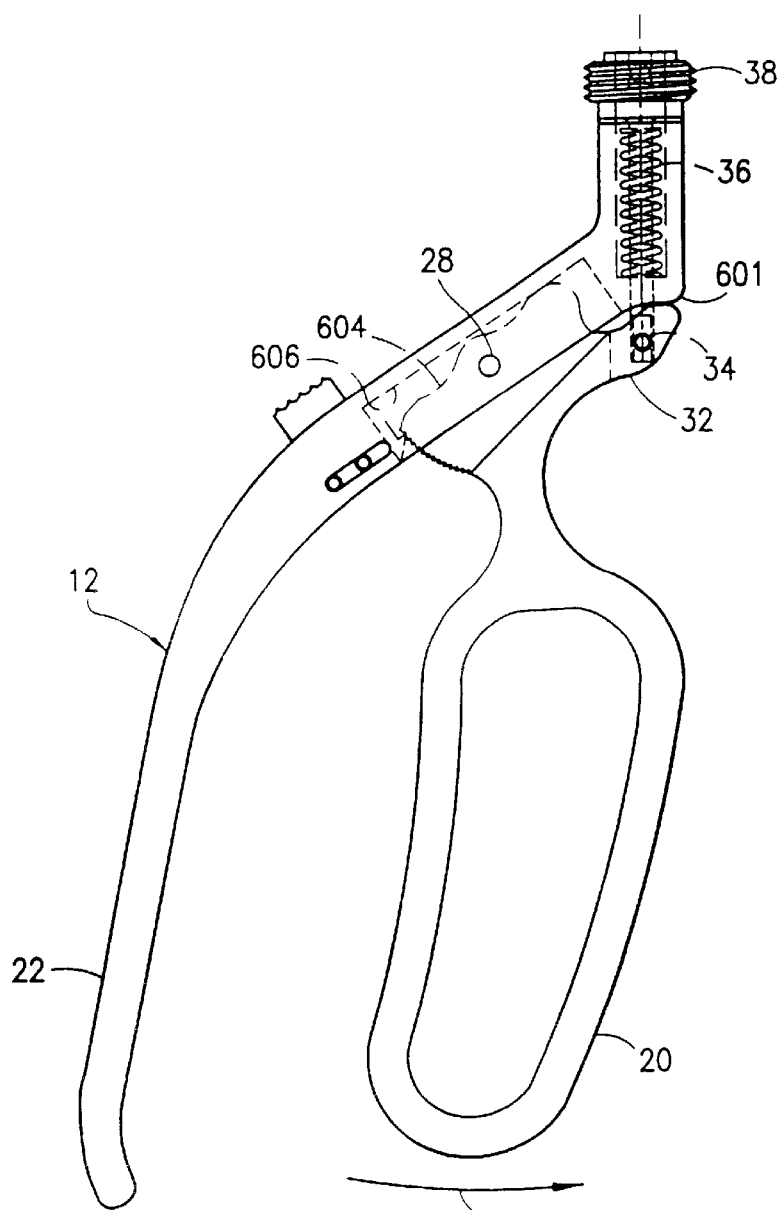
FIG. 23 diagrammatically illustrates a handle for the surgical instrument and one type of tactile response surface.

FIG. 23 diagrammatically illustrates handle 12. Handle 12 includes stationary grip member 22 and movable handle member 20. Movable member 20 is pivotally mounted to stationary member 22 via pivot pin or bolt 28. Stem 32 of movable member 20 is movably coupled to an actuator rod 34. Stem 32 is biased towards handle stop 601 due to biasing spring 36. Of course, other biasing mechanisms could be utilized such as leaf spring and pneumatic or hydraulic springs or mechanisms. In this manner, movable handle member 20 is biased in the "full open" direction shown by arrow 602.

Movable handle 20 includes a tactile response surface 604. In the illustrated embodiment, tactile response surface 604 is an undulated or wavy surface. Other types of tactile response surfaces could be utilized such as the fine tooth tactile surface shown in connection with FIG. 26. Tactile surface 604 could be a plurality of nubs or protrusions which ride on and bump against tactile response wall 606 of stationary handle member 22.

Figure 24:
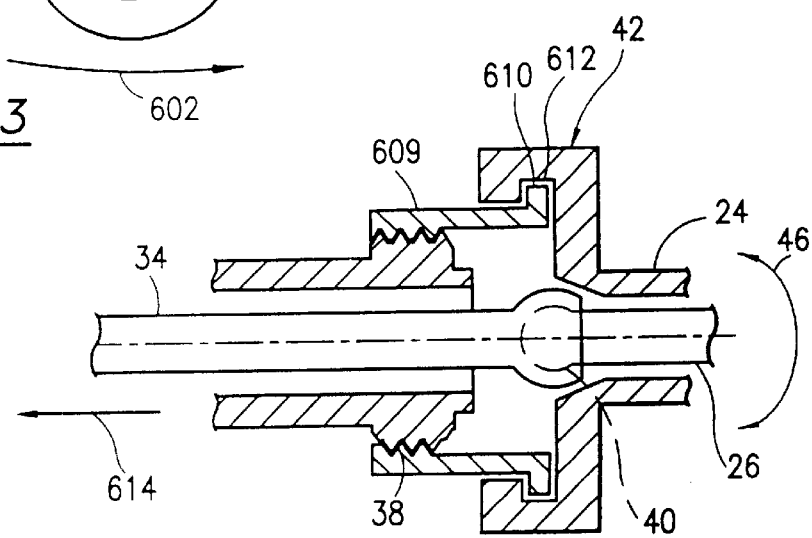
FIG. 24 diagrammatically illustrates the coupling between a handle actuator member and the longitudinally movable rod, and particularly shows the ability of the operator to rotate the elongated tube thereby rotating the attached end piece.

FIG. 24 diagrammatically illustrates details of the coupler section between handle 12 and the elongated tube 24 as well as the movable rod 26. Inboard handle segment has a male threaded joint 38 which threads onto a female threaded section 609. Female threaded section, at its inboard side, includes a rotatable coupling illustrated, in this embodiment, as a radially protruding ridge 610. Outer rotating coupling 42 forms a channel 612 within which is captured radially extending ridge 610. In this manner, the user can rotate female rotating unit 42 relative to male rotating coupler 610 as shown by the double headed arrow 46. This rotation in direction 46 rotates the elongated tube 24 and therefore rotates end piece 16 (see FIGS. 1 and 2).

Actuator rod 34, in this illustrated embodiment, includes a ball and socket joint within which ball 40 of movable rod 26 is placed. In this manner, when actuator 34 is retracted as shown by arrow 614, rod 26 is also retracted. The dimensions and the sizing of various components in FIG. 24 do not reflect actual size or dimensional relationships of the components. For example, movable rod 26 may be closely captured by tube 24. In this manner, rod 26 may have various types of cross-sectional configurations. However, the ability of the operator to rotate end piece 16 by rotating female coupler 42 may be affected by the cross-sectional configuration of rod 26.

In operation, when the operator compresses handle 20 towards stationary handle 22 (a direction opposite arrow 602), the user feels tactile response surface 604 as it bumps against response wall 606. Response wall 606 is defined in the stationary handle member 22. This informs the operator via tactile sensation that rod 26 has retracted to a certain linear position which may be compressed to first clip or close the blood vessel before cutting the blood vessel.

FIG. 25 diagrammatically illustrates a handle 12 for a surgical instrument. Handle 12 includes stationary grip member 22 and movable member 20. Movable member 20 is pivotally attached at pivot point 702 to stationary grip member 22. Handle 12 includes an operator control surface 704 which is explained in greater detail in FIGS. 26 and 27.

Handle 12 in FIG. 26 includes a movable member 20 having a tactile response surface 706 consisting of a plurality of fine teeth. Tactile response surface 706 abuts a responsive tactile piece 708 movably mounted in stationary grip member 22. Responsive tactile piece 708 is biased in the direction shown by arrow 709 towards tactile response surface 706. Spring 710 biases responsive tactile piece 708 towards tactile response surface 706. Other types of biasing mechanisms could be used such as leaf springs, U-shaped spring pieces, pneumatic and hydraulic springs. Also, responsive tactile piece 708 may be loosely mounted in stationary grip member 22 such that when movable handle member 20 is compressed or moved toward stationary handle member 22, responsive tactile piece 708 "jumps" or generates tactile and/or audible clicks every time a tooth or to a ridge on tactile response surface 706 passes complementary fine tooth point 712 on tactile response piece 708. Piece 708 in the illustrated embodiment is a movable block.

In the illustrated environment, spring 710 biases responsive tactile piece 708 towards tactile response surface 706. Tactile response piece 708 includes an operator control surface 704 which permits the operator to move response piece 708 rearward in the direction shown by arrow 714. This operator input counters the forward bias of the piece 78. The control surface is exposed to the operator and rises above handle member 22. By moving response piece 708 in the direction shown by arrow 704, complementary fine tooth detector 712 is moved away from tactile response surface 706 thereby eliminating any tactile response (or other response) based upon the compression of movable handle piece 20 towards stationary grip member 22. It should be remembered that when movable handle member 20 is compressed towards stationary grip member 22, actuator piece 34 retracts and further retracts rod 26, thereby closing the clip and subsequently closing the scissor jaws.

In the embodiment illustrated in FIG. 26, complementary fine tooth 712 on responsive tactile piece 708 and fine tooth ridges establishing tactile response surface 706 provide a ratchet set. Complementary fine tooth 712 has a 90° lagging tooth angle prohibiting movable handle member 20 to move outboard away from stationary handle member 22 when the ratchet is actuated. The other slope or leading edge of complementary fine tooth 712 is generally complementary to the leading angle of the plurality of fine tooth ridges on tactile response surface 706 such that movable handle member 20 can be compressed towards stationary grip member 22 without serious locking or latching of the complementary fine tooth 712 on the plurality of fine tooth ridges 704, 706.

Responsive tactile piece 708 also includes a latch or a lock as shown in FIG. 27 such that the operator can lock responsive tactile piece 708 in an OFF position This latch is provided by detent 720 which captures a complementary nub 722 upon full rearward retraction of piece 708 away from teeth 706. In addition, nub 722 provides a guide pin along with pin 724 to guide the responsive tactile piece 708 backwards and forwards in accordance with operator demands. In another embodiment, the latch may be configured at other points of travel of piece 708 in handle member 22.

It should be appreciated that the present invention includes a configuration where the responsive tactile piece is mounted to the movable handle and the tactile response surface is configured on the stationary grip. The mechanical reversal of these components is easily accomplished, i.e., the tactile piece may be mounted on stationary handle member 20 and the response surface defined on movable member 22. The claims appended hereto are meant to cover this configuration.

FIGS. 28a and 28b diagrammatically illustrate front end views and side views of appliance jaws with cam follower surfaces. The combination of FIGS. 28a, 28b diagrammatically illustrate appliance jaws 810 in a fully opened position; FIGS. 28c, 28d diagrammatically illustrate appliance jaws 810 partially closed; and the combination of FIGS. 28e, 28f diagrammatically illustrate the appliance jaws in a substantially closed position. The primary difference between cam actuated appliance jaws 810 and appliance jaws 16 (FIG. 11b-1) is the utilization of clip action cam follower surfaces rather than clip action cam follower channels. In FIGS. 28b, d and f, surgical appliance 492 includes a stationary tube or elongated member 1226 and a longitudinally movable cam actuator member 1340. Cam actuator member 1340 includes a forwardly disposed cam surface 812 which operates on cam follower surfaces 814 and 816 on the jaws. Clip action cam follower surface 814 is associated with jaw member 820. Cut action cam follower surface 816 is associated with scissor jaw 840. Lower jaw member 822 has a cam follower surface 824. Surfaces 814, 824 may be complementary shaped such that the jaw members 820, 822 close substantially simultaneously or may be dissimilar in shape resulting in different closure rates, times or closure positions dependent upon the longitudinal forward position of cam actuator member 1340. Jaw members 820, 822 are pivotally disposed about common lateral axis 825. Common lateral axis 825 is maintained in a stationary position with respect to elongated tube 1226 of surgical appliance 492. Cam actuator 1340 may have side slots for pivot pin 825 mounted on stationary tube 1226.

As cam actuator member 1340 moves longitudinally outboard, extending as shown by arrow 830, initially jaw members 820, 822 close and thereafter, scissor jaw members 840, 842 close. This is shown diagrammatically in FIG. 28d wherein cut action cam follower surface 816 includes a lateral extension or hump at that particular longitudinal position of movable rod or cam actuator member 1340. The longitudinal position of actuator 1340 is noted with respect to stationary rod or tube 1226. Essentially, cam actuator member forward surface 812 has not engaged the outboard extending surface of cut action cam follower surface 816 of scissor jaw members 840, 842 at that longitudinal extension position.

In FIG. 28f, cam actuator member surface 812 has effectively closed scissor jaws 840, 842 by acting upon lateral extensions or hump of the cut action cam follower surface 816 and its counterpart on follower 842. The front end view shown in FIGS. 28a, 28c and 28e show the start, intermediate and final cam clip and cut positions. FIG. 28c shows the scissor jaws laterally extended and the clip action jaws partially closed. It should be noted that multiple closure rates and times (based upon longitudinal extension positions) may be programmed or cut into or formed by the cam follower surfaces 816, 814.

FIGS. 29, 30 and 31 diagrammatically illustrate the principal elements of surgical appliance 492, a detailed view of the distal end of the surgical appliance when the appliance jaws are fully open and a detailed view of the distal end of the surgical appliance when the appliance jaws are partially closed. These figures illustrate another type of mechanical linkage to transfer handle movement into appliance jaw movement.

FIG. 29 shows handle members 450, 452 pivotally mounted about pivot point 1210 to each other. Upon compression and movement in the direction shown by arrows 454, 456, actuator tab 1212 of handle member 452 moves forward toward distal end 490 of surgical appliance 492. Forward movement of actuator member 1212 moves piston head 1214 in a forward direction, shown by arrow 1220. Piston head 1214 is mounted in a chamber 1222 and is mechanically coupled to actuator rod 1227. Piston head 1214 is biased in a rearward direction by spring member 1224 which is diagrammatically illustrated in FIG. 29.

Piston 1214 moves actuator pin 1227 longitudinally forward towards the appliance's distal end 490 with respect to outer static housing 1225. The pin 1227 is movably mounted in a static or stationary tube. This forward movement of actuator rod or pin 1227 with respect to static housing 1225 is applied to moveable rod 1228 and this motion is carried to distal end 1230 of handle section 1232, through coupler 1234, over an extended length portion of surgical appliance 492, diagrammatically illustrated as longitudinal length 1236, to the distal end region 1238. At distal end 1238, longitudinally moveable rod 1228 terminates and an appliance jaw casement member 1240 defines an outboard, elongated cavity 1242 within which is disposed appliance jaws 470, 472. The distal end of the jaws are spring loaded to pivot or flex in the casement 1240. In this embodiment, appliance jaws 470, 472 have inwardly extending base elements or legs 1250, 1252 which are joined together at joint 1254. Casement 1240 moves longitudinally with respect to static, elongated housing 1226.

FIG. 30 shows a detail view of distal end 1238 of surgical appliance 492. Essentially, longitudinally moveable tube element 1228 moves forward and aft in the direction shown by double headed arrow 1310 based upon the compression or release of handle members 450, 452. Of course, longitudinal movement of casement 1240 at rear end 1318 occurs with respect to the fixed position of static support tube 1226. Appliance jaws 470, 472 have outer or upper and lower cam surfaces 1312, 1314 which ride within the distal end portions 1340 of casement 1240. The shape of cam surfaces 1312, 1314 establish the speed and distance of closure of the clip jaws and scissor jaws (not shown). The slope of the cam surface relative to the appliance's axial centerline defines the speed of closure. The size or dimension (height) of the jaw and cam define one-half of the closure distance. The opposing jaw defines the other one-half of the closure distance. The speed and distance of closure of the clip jaws is directly related to the speed and distance of closure of a surgical clip retained by the jaws.

Appliance jaws 470, 472 are defined at the distal end of extend elements 1250, 1252 of casement 1240. Elements 1250, 1252 are joined together at point 1254. To secure jaw appliance elements 1250, 1252, a pin, bolt or other lateral mount 1316 extends through the base of appliance jaw elements 1250, 1252 through channel 1319 and into the static, non-moveable tubular housing 1226. Jaw casement 1240 may include a male threaded element 1320 at its proximal end 1318 which threadably attaches to a female threaded element 1322 at the distal end of moveable rod 1228. Movable rod 1228 rides within static support tube 1226 and further motivates appliance jaw casement 1240. Appliance jaw casement 1240 has a strong distal end segment 1340 which resists lateral, outboard force of the clip carrying jaws.

Upon forward movement of actuator tab 1212 of handle member 452, piston 1214 impacts lead pin 1227. Lead pin 1227 forces movable rod 1228 to move forward in direction shown by arrow 1220. See FIG. 30. Rod 1228 is enclosed by a stationary or static tube 1225.

FIG. 31 shows rod 1228 terminating in a screw thread plug 1322. Threaded plug 1322 is mounted to proximal, threaded end 1320 of movable casement 1240. Jaw appliance extender elements 1250, 1252 are fixed with respect to outer static tube 1226 via lateral pin or mount 1316. However, jaw casement 1240 moves forward due to the forward movement of movable rod 1228. This forces the distal end element 1340 of casement 1240 to move forward in direction 1342 shown in FIG. 31. As a result, the forward movement of distal end 1340 of casement 1318 causes closure of appliance jaws 470, 472. Jaws 470, 472 are fixed with respect to outer static tube 1226. Essentially, casement end 1340 acts on cam surfaces 1312, 1314 of appliance jaws 470, 472. Clip 471 is collapsed upon itself in FIG. 31.

Other types of mechanical linkage elements may be utilized to affect closure of appliance jaws 470, 472.

Further, surgical appliance 492 may be equipped with automated surgical clip loaders. The following patents show automated surgical clip loaders and the content of these patents is incorporated herein by reference thereto.

3,665,924 to Noiles
3,675,688 to Bryan
3,735,762 to Bryan
3,740,994 to DeCarlo
3,819,100 to Noiles
3,955,581 to Spasiano et al.
4,086,926 to Green et al.
5,032,127 to Frazee et al.
5,049,152 to Simon et al.
5,104,394 to Knoepfler
5,192,288 to Thompson et al.
U.S. Pat. No. 5,269,792 to Kovac et al.
U.S. Pat. No. 5,336,229 to Noda
U.S. Pat. No. 5,447,513 to Davison et al.
U.S. Pat. No. 5,527,319 to Green et al.
U.S. Pat. No. 5,601,573 to Fogelberg et al.

A further example of a surgical appliance wherein a moveable tube operates on the outer surface of appliance jaw is shown in U.S. Pat. No. 3,777,538 to Weatherly et al.

Figure 32:
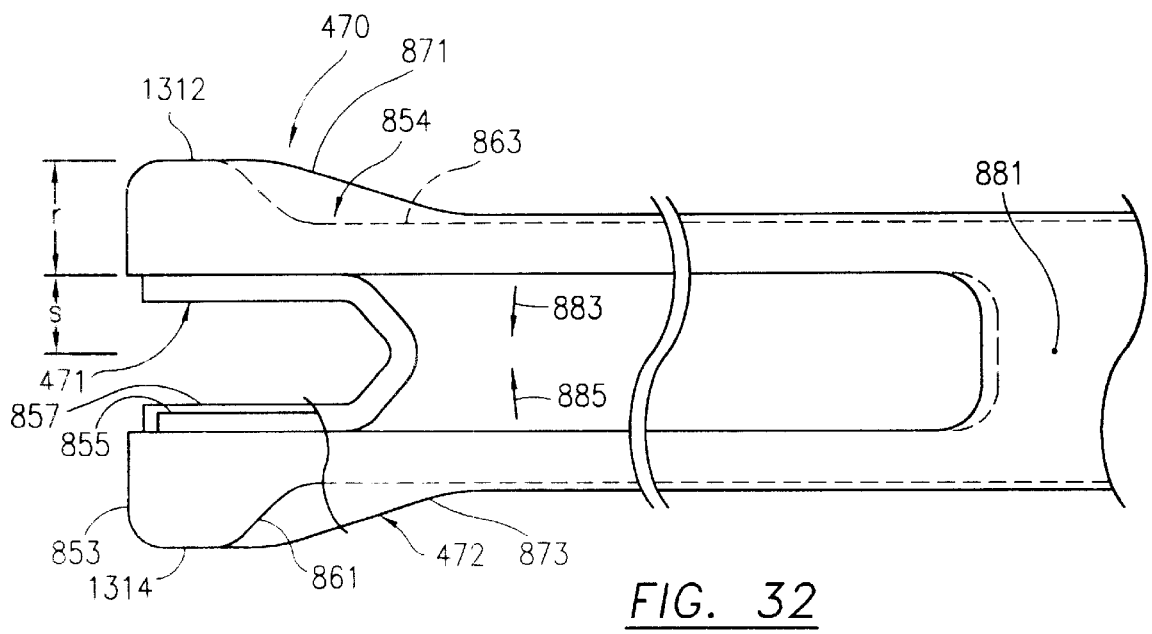
FIG. 32 shows a detail, side view of the clip carrying jaw and scissor jaw with outer cam action follower surfaces and flexible jaw inboard elements.

FIG. 32 diagrammatically illustrates appliance jaws 470, 472 and particularly the distal end of those jaws and cam follower surfaces 1312, 1314. A surgical clip 471 is mounted in clip carrying channels (not shown) present in the mouth defining portions of the appliance jaws 470, 472. Lower appliance jaw 472 is partially broken away to reveal lower scissor jaw member 853. Lower scissor jaw member 853 carries a scissor blade 855 thereon. A second surgical clip 857 is illustrated laterally behind scissor blade 855.

Scissor jaw 853 and its opposite jaw member 854 are closed based upon cut action cam follower surfaces 861, 863. The cut action cam follower surfaces 861, 863 are activated by the cam actuator member (member 1340 of casement 1240 in FIG. 31) at a later time (a more forward position) as compared with clip action cam follower surfaces 871, 873. Appliance jaws 470, 472 effectively pivot about an imaginary point 881 at a rear end of the appliance jaw system. In this sense, pivoting in the direction shown by arrows 883, 885 is achieved due to the relatively long length of the extender members of the appliance jaws. The flexing of long length jaw extenders is mechanically similar to pivot action. The length of appliance jaws is diagrammatically illustrated in FIGS. 30 and 31 above. See extender members 1250, 1252 in FIG. 31.

It should be noted that longitudinally movable tube 1340 (FIGS. 28b, d and f) and casement 1240 (FIG. 31) may have a "square" distal end to match a "squared off" cam follower surfaces of appliance jaws 470, 472, may be elliptical in shape or may be round in shape. If the interior shape of movable extending tube 1340, 1240 is elliptical or round, the cam follower surfaces 820, 822, 816 (FIG. 28b) or 1312, 1314 (FIG. 31) have a complimentary shape.

Figure 33:
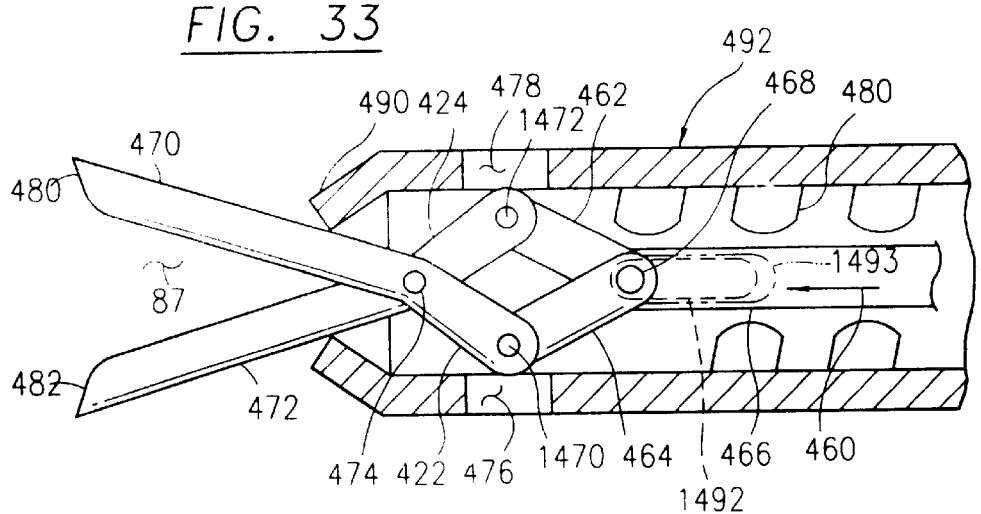
FIG. 33 diagrammatically illustrates a surgical appliance for utilizing the multiple surgical clips.

FIG. 33 diagrammatically illustrates another type of mechanical linkage to transfer compressive force 454, 456 (FIG. 29) into appliance jaw compressive force to close appliance jaws 470, 472 on the longitudinally disposed clips (not shown). In this embodiment, the compressive force is converted into longitudinally directed motion and force 460. Appliance jaws 470, 472 pivot about point 474. The jaws have aft extending members 422, 424. Mechanical linkage members 462, 464 are connected at their proximal end to longitudinally moveable bar or rod 466. Mechanical links 462, 464 are rotatably mounted at point 468 to longitudinally moveable bar 466. When bar or rod 466 moves aft away from distal end 490 of surgical appliance 492, as shown by arrow 460, mechanical linkage bars 462, 464 transfer that longitudinal movement into lateral, closing movement of appliance jaw extenders 422, 424. This lateral closing movement is achieved due to the mechanical and rotative connection at linkage points 1470 and 1472 of jaw extenders 422, 424. Surgical appliance 492 has cutouts 476, 478 which pennit jaw extenders 422, 424 to extend laterally outward with respect to the surgical appliance 492 when bar 466 moves forward or opposite arrow 460. When jaw extenders 422, 424 move laterally inboard due to the mechanical linkage conversion of longitudinal aft movement (direction 460) into lateral inboard movement, the distal ends 480, 482 of appliance jaws 470, 472 close, thereby collapsing the clips. Of course, forward longitudinal movement in a direction opposite arrow 460 causes mechanical links 462, 464 to push jaw extenders 422, 424 laterally outboard away from the axial centerline of surgical appliance 492. This mechanical conversion of longitudinal force and direction into outboard lateral force causes appliance jaws 470, 472 to open with respect to each other. Surgical appliance 492 may be threadably attached to the end piece which has female threads 480. Compressive force on the surgical appliance handle members can be converted into rearward longitudinal movement 460 by simple mechanical systems.

In order to achieve the cutting of the blood vessel or organic structure subsequent to the clipping operation (the application of surgical clips by jaws 470, 472 on the target structure), the scissor jaws have extenders similar to extenders 424, 422 and have mechanical links similar to links 462, 464 except the scissor mechanical links have longitudinally aligned segments 1493 extending aft in the direction of arrow 460 and these link segments include longitudinal cut-outs 1492 within which link pin 468 travels. When pin 468 is in the forward position of the cut-out 1492 and the rod 466 is pushing forward, the scissor jaws open concurrently with the clip jaws. When the rod 466 first moves aft in the direction of arrow 460, the clip jaws 470, 472 close but the pin 468 moves in the longitudinal channel of the cut-out 1492 of each scissor jaw mechanical link extender 1493. When the pin 468 reaches the aft position in the cut-out 1492, the pin then pulls the scissor mechanical links laterally inboard, thereby closing the scissor jaws at a time subsequent to the closure of the clip jaws.

Figure 34:
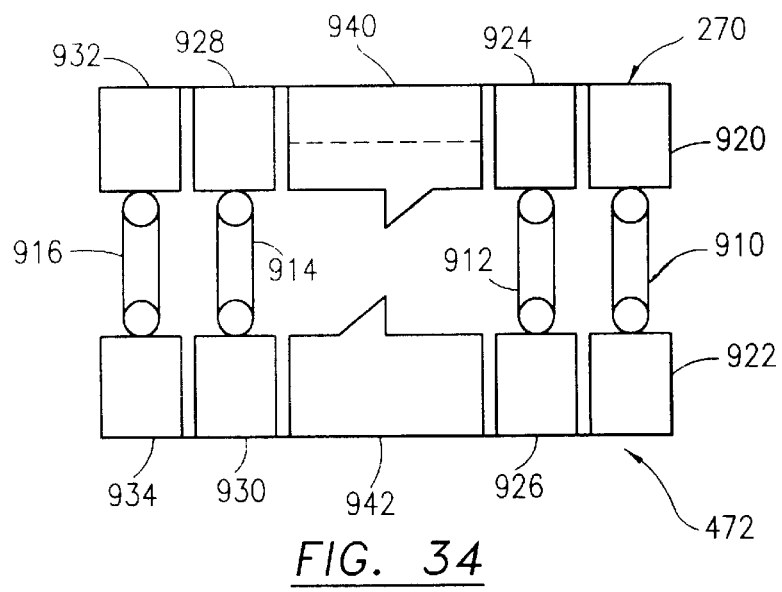
FIG. 34 diagrammatically illustrates a system with multiple clip carrying jaws.

FIG. 34 diagrammatically illustrates an end view of appliance jaws 470, 472 wherein a plurality of surgical clips are retained by jaw set. In the previously illustrated embodiments, appliance jaws 470, 472 (which includes the scissor jaw set 940, 942), utilize generally a pair of surgical staple clips. However, the present invention and the concepts and constructions discussed herein can be carried forward into multiple clip surgical appliances. FIG. 34 shows surgical clip 910 disposed in clip channels of jaw members 920 and 922. Clip 912 is disposed in a clip carrying channel of jaw member 924 and another clip carrying channel in jaw member 926. Clip 914 is disposed in opposing clip channels of jaw members 928, 930. Clip 916 is disposed opposing clip channels in jaw member 932 and jaw member 934. Scissor jaw member 940 cooperates with the lower scissor jaw member 942.

It should be noted that although it may convenient and preferable to locate scissor jaw members 940, 942 at an intermediate position between clips 910, 912 on the right-hand side and clips 914, 916 on the left hand side, it is not required to locate scissor jaw members 940, 942 at that intermediate position. There may be instances in particular surgical procedures wherein all the clips would be located on one side or a majority of the clips would be located on one side and scissor jaw members 940, 942 would be located on the other side. Specifically with respect to FIG. 34, clips 910, 912 and 914 may be located adjacent to each other and scissor jaw members 940, 942 may be disposed intermediate clip 914 and clip 916. In this manner, the medical professional would attach three clips on one side of the blood vessel or other organic structure, cut the blood vessel or organic structure on one end of that three clip system and clip the blood vessel or other organic structure with the remaining outboard clip 916. In a similar manner, scissor jaws 940, 942 may be disposed at one lateral end of one or more of a series of surgical clips 910, 912, 914 and 916. In all of these embodiments, the surgical appliance operates in the same manner, to wit, the surgical clip is first "clipped onto" the blood vessel or other organic structure and then, at a subsequent time, the blood or organic structure is cut by scissor jaws 940, 942.

Clip jaw members 920, 922 may form a singular clip jaw set with independent, opposing and closeable jaw members. Alternatively, lower clip jaw members 922, 926 may form one clip jaw set and upper clip jaw members 920, 924 may form a second clip jaw set. Independent jaw members are shown in FIG. 28b. Conjoint or ganged clip jaw sets are shown in FIG. 5. The term "clip jaw set" includes independent, opposing jaw members and conjointly configured or ganged jaw members.

Figure 35:
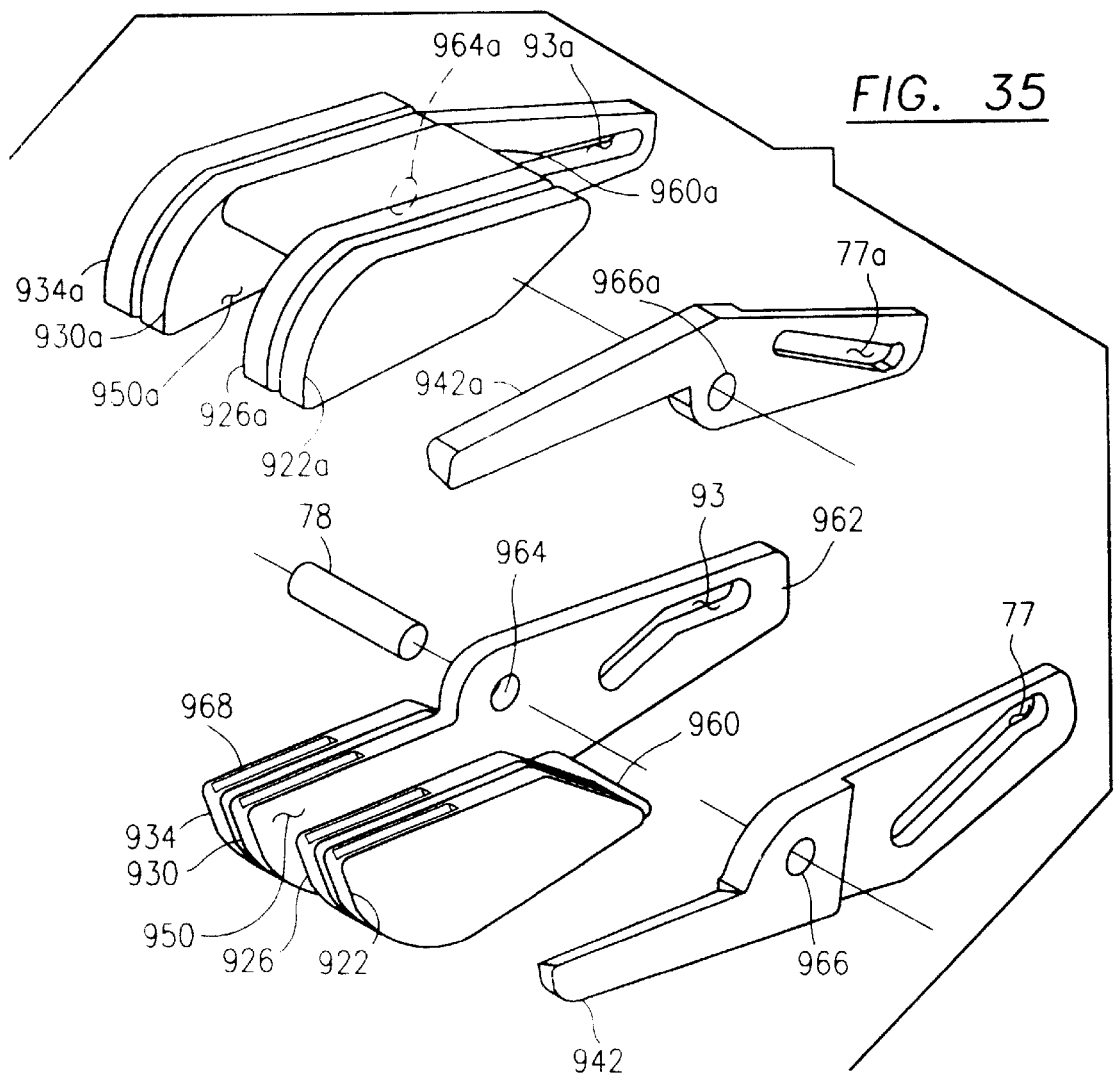
FIGS. 35, 36 and 37 diagrammatically illustrate multiple clip jaw appliances (with cam follower channels and cam follower surfaces).
Figure 36:
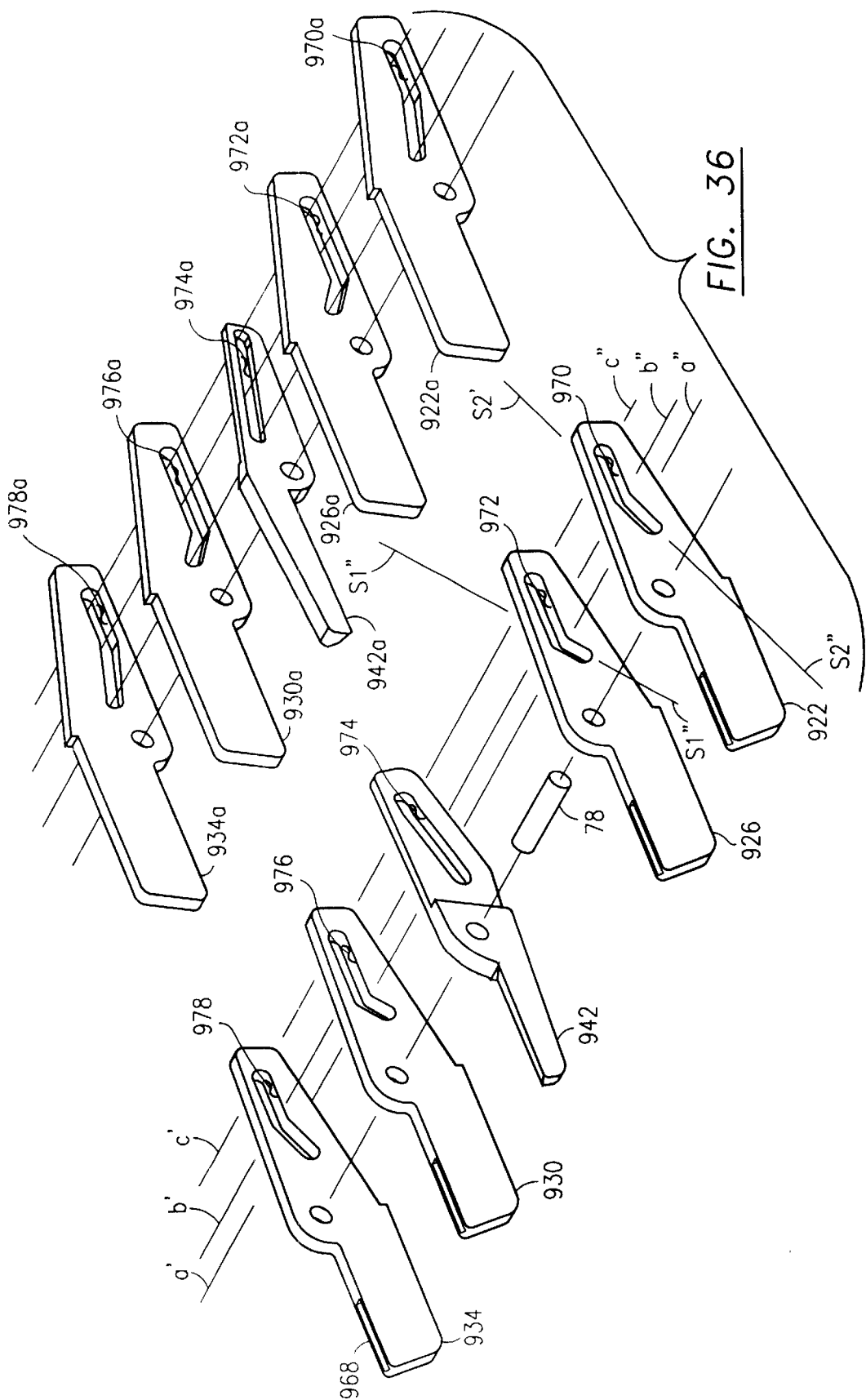

FIG. 35 diagrammatically illustrates a ganged clip jaw set for lower clip jaw members. FIG. 36 diagrammatically illustrates independent clip jaw members retaining multiple clips. Both FIGS. 35 and 36 show multiple clip systems.

FIG. 35 diagrammatically illustrates clip jaw members 922, 926, 930 and 934 mounted together or mounted conjointly via base member 960. Base member 960, in the illustrated embodiment, extends along the back side of jaw members 922, 226, 930 and 934. These jaw members rotate conjointly based upon the longitudinal position of a cam pin (not shown) in cam follower channel 93 defined on rearward extending plate 962 of the jaw set. Common lateral axis pin 78 extends through aperture 964 and 966. Aperture 966 is defined by lower scissor jaw member 942. Scissor jaw member 942 is rotated about common lateral axis 78 based upon the lateral position of a cam pin (not shown) traveling in cut action cam follower channel 77.

The clip carrying channels, one of which is clip carrying channel 968 on jaw member 934, are illustrated in the figure. The scissor blade of scissor jaw 942 is disposed in gap 950. FIG. 35 also shows upper clip jaw members 922a, 926a, 930a and 934a. Upper jaw member 922a cooperates with lower jaw member 922 and pinches the clip held in clip groove or channel on the mouth of the jaw set. Scissor jaw 942a cooperates with lower scissor jaw 942 to cut the blood vessel. Cam follower channels 93a and 77a operate in the manner discussed above in connection with follower channels 93, 77.

FIG. 36 diagrammatically illustrates independently configured jaw members 922, 926, 930 and 934. Each one of these independently configured jaw members includes a clip carrying channel, one of which is clip carrying channel 968 in jaw member 934. Although scissor jaw member 942 is illustrated in an intermediate position between clip jaw members 922, 926 on the right side and clip jaw members 930, 934 on the left side, scissor jaw 942 can be moved to the far left side, or moved intermediate clip jaws 934, 930, or intermediate jaw members 926, 922 or on the far right side.

Each jaw member and scissor jaw includes a cam follower channel. From right to left, these cam follower channels are channels 970, 972, 974, 976 and 978. However, the cam follower channels have "break point" or are discontinuous in their respective linear aspects at different points. Accordingly, channels 972, 976 cause clip jaw members 926, 930 to close and collapse a surgical clip prior to the closure of the clip retained in jaw members 922, 934. The discontinuous linear break point for channels 972, 976 is located at angular planar position a'–a". Clip jaw members 922, 934 compress the clip retained in the clip carrying channels faster as compared with jaws 926, 930 since channels 970, 978 have a discontinuous linear point at plane b'–b". This lateral break point plane is at a position which is more rearward than the cam pin plane position for channels 972, 976 and the break point on lateral plane a'–a".

The rate of closure or speed of closure of clip jaw members 926, 930 is established by the slope S1'–S1" in the forward portion of cam follower channels 972, 976. Accordingly, the slope of initial or forward channel portion established at line or plane S1'–S1" is steeper than the slope on the forward portion of channels 970, 978 as shown by line or plane S2'–S2". Clip jaw members 926, 930 close faster than clip jaw members 922, 934. In a similar manner, the slope of the forward linear portion of cam follower channel 974 and scissor jaw member 942 is less than the slope of planes S1 and S2. Slope is measured with respect to the longitudinal axis of the appliance. Hence, the scissor closes subsequent to closure of clip jaw members 922, 934. FIG. 36 also shows upper jaw members 922a, 926a, 930a and 934a and shows upper scissor jaw member 942a as well as cam follower channels 970a, 972a, 976a, 978a and 974a for the jaw members and scissor jaw member.

In sequential operation, the surgical appliance first collapses the surgical clip retained jaw members 926, 930, then collapses the clip held by jaw members 922, 934 and subsequently cuts the blood vessel or organic structure with scissor jaw 948. Similar cam follower channels are normally used in connection with the coordinated closure of independent jaw members or several different sets of ganged together jaw members. FIG. 35 shows jaw members 922, 926, 930 and 934 ganged together and operating as a singular closeable unit. A lower, ganged jaw set is aligned with an upper, ganged jaw set and both ganged sets have similar cam follower channels. If the surgical appliance includes multiple lower ganged jaw members (and multiple upper ganged sets), the clips closeable on the blood vessel or other organic are placed on the blood vessel or structure at different times based upon the different shapes and configurations of the cam follower channels 970, 972, 974, 976 and 978 shown with respect to independent jaw member plates.

Figure 37:
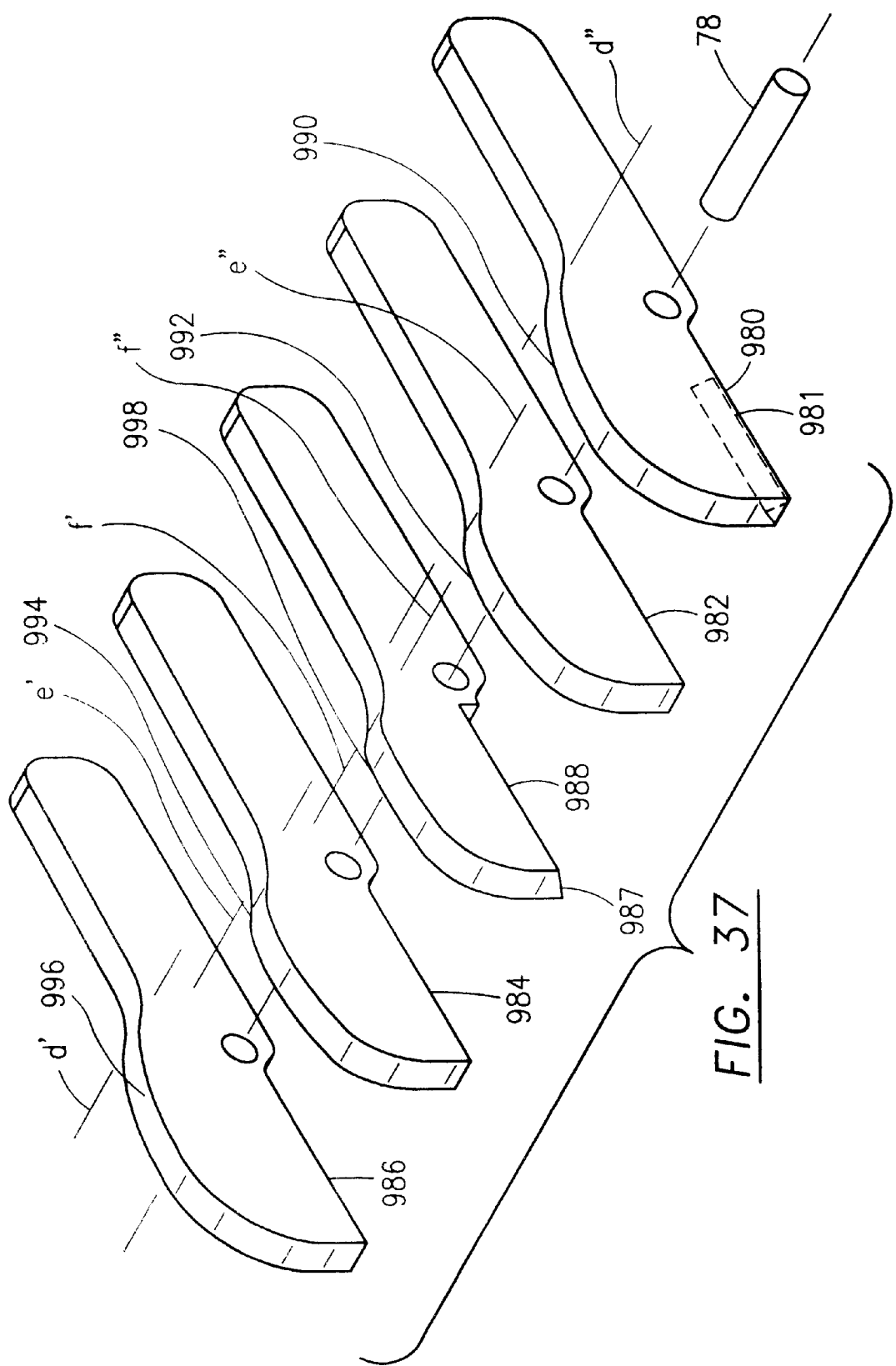

FIG. 37 diagrammatically illustrates a plurality of clip jaw members 980, 982, 984, 986 which collectively define the upper jaw members of a surgical appliance. FIG. 38 diagrammatically illustrates lower jaw members of a surgical appliance. Scissor jaw member 988 includes a blade 987 which is utilized to cut a blood vessel or other organic structure. A clip is placed in an appropriately shaped clip carrying channel, one of which is clip carrying channel 981 on clip jaw member 980. The clip jaw members and the scissor jaw member 988 rotate about a common lateral axis 78. A pin runs through the axis.

Clip jaw members 980, 986 have clip action cam follower surfaces 990, 996 which are substantially similar. The cam follower surfaces 990, 996 are initially activated when the cam actuator member 1340 (FIG. 28b) rides over the cam follower surface and particularly when the actuator member reaches the plane d'–d". At that longitudinal position of the actuator member (with respect to fixed common lateral axis 78), the actuator member forces clip jaw members 980, 986 to close thereby collapsing the surgical clip retained in the clip channels. At a subsequent time, the cam actuator member reaches plane e'–e" which begins the actuation phase of cam follower surfaces 992, 994 associated with clip jaw members 982, 984. At a subsequent time, the cam actuator member reaches plane f'–f" and begins affecting the closure of scissor jaw member 988 by acting on cam follower surface 998. From a fixed position, plane d is rearwardly disposed, plane e is intermediate and plane f is forwardly disposed. The comparison of FIGS. 36 and 37 show that the cam follower channels and the surfaces can be configured to achieve different closure rates at different times (different longitudinal positions) for different clips. Further, as described earlier, the scissor jaws can be positioned at any appropriate lateral position on common lateral axis 78. Further, the cam follower surfaces 990, 992, 994, 996 and 998 are configured on the upper and lower jaw member or jaw set surfaces. FIG. 38 shows cam follower surfaces 980a, 992a, 998a, 994a 996a respectively associated with members 980a, 982a, 998a, 984a and 986a which operate as discussed above in connection with cam follower surfaces 990, 992, 994, 996 and 998. Rather than rotate around a common lateral axis 78, these cam follower surfaces 990, 992, 994, 996 can be defined in a flexible element diagrammatically illustrated in FIG. 32. In FIG. 32, the jaw members close based upon flexing about point 881 at a rearward position with respect to the distal end of the surgical appliance.

The claims appended hereto are meant to cover modifications and changes within the scope and spirit of the present invention.

What is claimed is:

1. A surgical instrument for stapling with surgical clips and cutting a blood vessel or other organic structure comprising:

an elongated tube having a proximal end and a distal end, said tube having a longitudinally movable rod disposed therein;

a handle mounted on said proximal end of said tube, said handle having a movable member coupled to said movable rod which longitudinally moves said rod with respect to said tube upon actuation of said movable member;

at least one pair of surgical staple clip carrying jaw sets, each clip jaw set having two jaw members which pivot about a common lateral axis located at said distal end of said elongated tube, each jaw member defining a clip channel at its jaw mouth at least one scissor jaw set having upper and lower, opposing scissor jaw members which pivot about said common lateral axis;

a longitudinally extending cam actuator member mounted on said distal end of said moveable rod;

each clip jaw set defining a clip-action cam follower surface and said scissor jaw set defining a cut-action cam follower surface, said longitudinally extending cam actuator member movable with respect to said clip-action and cut-action cam follower surfaces and said clip-action cam follower surfaces shaped to initially close said clip jaw sets and said cut-action cam follower surfaces shaped to subsequently close said scissor jaw set and cut said blood vessel or other organic structure upon longitudinal movement of said longitudinally extending cam actuator member.

2. A surgical instrument as claimed in claim 1 wherein said clip jaw sets and scissor jaw set are rotatably mounted at a stationary position with respect to said common lateral axis and said elongated tube, said longitudinally extending cam actuator member movably protruding beyond said distal end of said elongated tube and traveling over said clip-action and cut-action cam follower surfaces of said clip jaw sets and said scissor jaw set.

3. A surgical instrument as claimed in claim 1 wherein each clip jaw member has a respective clip-action cam follower surface.

4. A surgical instrument as claimed in claim 3 wherein said clip-action and cut-action cam follower surfaces are disposed on outboard, exterior edges of each jaw member and on outboard, exterior edges of said scissor jaw members.

5. A surgical instrument as claimed in claim 1 wherein said one pair of clip carrying jaw sets is a first and a second clip jaw set, said first and second clip jaw sets respectively define an upper clip jaw set and a lower clip jaw set with at least two conjoint upper jaw members and at least two conjoint lower jaw members, said upper and lower jaw sets oppositely disposed at an appliance jaw mouth, and said upper and lower clip jaw sets define respective ones of said clip-action cam follower surfaces.

6. A surgical instrument as claimed in claim 4 wherein said clip-action and cut-action cam follower surfaces are disposed on outboard, exterior edges of at least one jaw member of a respective clip jaw set and on outboard, exterior edges of said scissor jaw members.

7. A surgical instrument for stapling, with a plurality of surgical clips, and cutting a blood vessel or other organic structure comprising:
   an elongated tube having a proximal end and a distal end, said tube having a longitudinally movable rod disposed therein;
   a handle mounted on said proximal end of said tube, said handle having a movable member coupled to said movable rod which longitudinally moves said rod with respect to said tube upon actuation of said movable member;
   a plurality of pairs of clip carrying jaw sets for said plurality of clips each clip jaw set having two opposing jaw members which pivot towards each other about a common lateral axis disposed at said distal end of said elongated tube, each clip jaw member defining a clip channel at its jaw mouth;
   at least one scissor jaw set having upper and lower, opposing scissor jaw members which pivot about said common lateral axis;
   a longitudinally extending cam actuator member mounted on said distal end of said movable rod;
   each clip jaw member defining a respective clip-action cam follower surface and each scissor jaw member defining a respective cut-action cam follower surface, said longitudinally extending cam actuator member movable with respect to said clip-action and cut-action cam follower surfaces and said clip-action cam follower surfaces shaped to initially close said plurality of clip jaw sets and said cut-action cam follower surfaces shaped to subsequently close said scissor jaw set to sequentially and pluralistically clip and then cut said blood vessel or other organic structure upon longitudinal movement of said longitudinally extending cam actuator member.

8. A surgical instrument as claimed in claim 7 wherein said clip jaw sets and scissor jaw set are rotatably mounted at a stationary position with respect to said common lateral axis and said elongated tube, said longitudinally extending cam actuator member movably protruding beyond said distal end of said elongated tube and traveling over said clip-action and cut-action cam follower surfaces of said clip jaw sets and said scissor jaw set.

9. A surgical instrument as claimed in claim 7 wherein at least one clip jaw set and its corresponding clip jaw members have respective clip-action cam follower surfaces that are differently shaped than other clip jaw sets of said plurality of clip jaw sets such that said one clip jaw set closes at a different longitudinal position than said other clip jaw sets of said plurality of clip jaw sets.

10. A surgical instrument as claimed in claim 9 wherein said clip-action and cut-action cam follower surfaces are disposed on outboard, exterior edges of each jaw member of a respective clip jaw set and on outboard, exterior edges of said scissor jaw members.

11. A surgical instrument as claimed in claim 10 wherein each clip jaw set is adapted to retain a single surgical clip in said respective clip channels in corresponding jaw member mouths, and each respective clip jaw set and corresponding jaw members with corresponding clip-action cam follower surfaces have substantially similar cam shapes and wherein clip-action cam follower surfaces of a respectively different clip jaw set have substantially different cam shapes whereby said similar cam shapes cause closure at similar times and said different cam shapes cause closure at different times during said longitudinal movement of said cam actuator member.

12. A surgical instrument as claimed in claim 7 wherein said scissor jaw set is disposed at an intermediate position between said plurality of clip jaw sets.

13. A surgical instrument for stapling, with a plurality of surgical clips, and cutting a blood vessel or other organic structure comprising:
   an elongated tube having a proximal end and a distal end, said tube having a longitudinally movable rod disposed therein;
   a handle mounted on said proximal end of said tube, said handle having a movable member coupled to said movable rod which longitudinally moves said rod with respect to said tube upon actuation of said movable member;
   a plurality of clip carrying jaw sets defining lower jaw sets and upper jaw sets, each clip jaw set having at least two laterally disposed clip jaw members which are ganged together and pivot about a common lateral axis disposed at said distal end of said elongated tube, each clip jaw member defining a clip channel at its jaw mouth and each lower jaw set disposed at an opposing position relative to a corresponding upper jaw set;
   at least one scissor jaw set having upper and lower, opposing scissor jaw members which pivot about said common lateral axis;
   a longitudinally extending cam actuator member mounted on said distal end of said movable rod;
   each clip jaw set defining a clip-action cam follower surface and each scissor jaw member defining a respective cut-action cam follower surface, said longitudinally extending cam actuator member movable with respect to said clip-action and cut-action cam follower surfaces and said clip-action cam follower surfaces shaped to initially close said plurality of clip jaw sets and said cut-action cam follower surfaces shaped to subsequently close said scissor jaw set to sequentially and pluralistically clip and then cut said blood vessel or other organic structure upon longitudinal movement of said longitudinally extending cam actuator member.

14. A surgical instrument as claimed in claim 13 wherein said clip-action and cut-action cam follower surfaces are disposed on outboard, exterior edges of at least one jaw member of a respective clip jaw set and on outboard, exterior edges of said scissor jaw members.

15. A surgical instrument as claimed in claim 13 wherein each upper clip jaw set coacts with a corresponding opposing lower clip jaw set such that ganged closure of opposing clip jaw members occurs due to substantially similar cam shapes on the corresponding clip-action cam follower surfaces of corresponding upper and lower clip jaw sets, and wherein clip-action cam follower surfaces of a respectively different ganged clip jaw set of said plurality of clip jaw sets have substantially different cam shapes whereby said similar cam shapes cause closure at similar times and said different cam shapes cause closure at different times during longitudinal movement of said cam actuator member.

16. A surgical instrument for stapling, with a plurality of surgical clips, and cutting a blood vessel or other organic structure comprising:

an elongated tube having a proximal end and a distal end, said tube having a longitudinally movable rod disposed therein;

a handle mounted on said proximal end of said tube, said handle having a movable member coupled to said movable rod which longitudinally moves said rod with respect to said tube upon actuation of said movable member;

a plurality of pairs of clip carrying jaw sets corresponding to said plurality of clips, each clip jaw set having two opposing jaw members which pivot towards each other about a common lateral axis disposed at said distal end of said elongated tube, each clip jaw member defining a clip channel at its jaw mouth;

at least one scissor jaw set having upper and lower, opposing scissor jaw members which pivot about said common lateral axis;

a laterally extending cam mounted on said distal end of said movable rod;

each clip jaw member defining a respective clip-action cam follower channel and each scissor jaw member defining a respective cut-action cam follower channel, said laterally extending cam disposed in said clip-action and cut-action cam follower channels and said clip-action cam follower channels shaped to initially close said plurality of clip jaw sets and said cut-action cam follower channels shaped to subsequently close said scissor jaw set to sequentially and pluralistically clip and then cut said blood vessel or other organic structure upon longitudinal movement of said laterally extending cam.

17. A surgical instrument as claimed in claim 16 wherein at least one clip jaw set and its corresponding clip jaw members have respective clip-action cam follower channels that are differently shaped than other clip jaw sets of said plurality of clip jaw sets such that said one clip jaw set closes at a different longitudinal position of said laterally extending cam than said other clip jaw sets of said plurality of clip jaw sets.

18. A surgical instrument as claimed in claim 16 wherein each clip jaw set is adapted to retain a single surgical clip in said respective clip channels in corresponding jaw member mouths, and each respective clip jaw set and corresponding jaw members with corresponding clip-action cam follower channels have substantially similar cam shapes and wherein clip-action cam follower channels of a respectively different clip jaw set have substantially different cam shapes whereby said similar cam shapes cause closure at similar times and different cam shapes cause closure at different times during said longitudinal movement of said cam.

19. A surgical instrument as claimed in claim 16 wherein said scissor jaw set is disposed at an intermediate position between said plurality of clip jaw sets.

20. A surgical instrument for stapling, with a plurality of surgical clips, and cutting a blood vessel or other organic structure comprising:

an elongated tube having a proximal end and a distal end, said tube having a longitudinally movable rod disposed therein;

a handle mounted on said proximal end of said tube, said handle having a movable member coupled to said movable rod which longitudinally moves said rod with respect to said tube upon actuation of said movable member;

a plurality of clip carrying jaw sets defining lower jaw sets and upper jaw sets, each clip jaw set having at least two laterally disposed clip jaw members which are ganged together and pivot about a common lateral axis disposed at said distal end of said elongated tube, each clip jaw member defining a clip channel at its jaw mouth and each lower jaw set disposed at an opposing position relative to a corresponding upper jaw set;

at least one scissor jaw set having upper and lower, opposing scissor jaw members which pivot about said common lateral axis;

a laterally extending cam mounted on said distal end of said movable rod;

each clip jaw set defining a clip-action cam follower channel and each scissor jaw member defining a respective cut-action cam follower channel, said laterally extending cam disposed in said clip-action and cut-action cam follower channels and said clip-action cam follower channels shaped to initially close said plurality of clip jaw sets and said cut-action cam follower channels shaped to subsequently close said scissor jaw set to sequentially and pluralistically clip and then cut said blood vessel or other organic structure upon longitudinal movement of said laterally extending cam.

21. A surgical instrument as claimed in claim 20 wherein each upper clip jaw set coacts with a corresponding opposing lower clip jaw set such that ganged closure of opposing clip jaw members occurs due to substantially similar cam shapes on the corresponding clip-action cam follower channels of corresponding upper and lower clip jaw sets, and wherein clip-action cam follower channels of a respectively different ganged clip jaw set have substantially different cam shapes whereby said similar cam shapes cause closure at similar times and said different cam shapes cause closure at different times during longitudinal movement of said cam.

22. A method for surgically stapling and cutting a segment of a blood vessel or other organic structure in a body with an elongated surgical instrument having an elongated movable rod therein extending from an outboard, proximal position to a distal end near a surgical site in said body, said surgical instrument carrying a plurality of surgical staple clips at said distal end of said rod, the method comprising the steps of:

longitudinally moving said rod in a substantially singular, operative stroke;

during said single operative stroke:
- sequentially clipping said segment of blood vessel or other organic structure with at least one of said plurality surgical staple clips and then clipping said segment of blood vessel or other organic structure with at least one or more of a remainder of said plurality surgical staple clips during a first portion of said singular operative stroke; and
- subsequently cutting said segment of blood vessel or other organic structure during a second portion of said singular operative stroke.

23. A method as claimed in claim 22 wherein said singular operative stroke is caused by a single, generally uniform extension of said rod towards said distal end.

24. A method as claimed in claim 23 wherein said surgical instrument defines a common axis at said distal end and wherein said clipping and cutting steps include the step of translating said singular longitudinal movement of said rod into sequential plural pivotal movements about said common axis.

25. A method as claimed in claim 24 wherein said surgical staple clips are generally U-shaped and the method includes the step of sequentially collapsing said U-shaped clips onto said segment during said first portion of said operative stroke.

26. A method for surgically stapling and cutting a segment of a blood vessel or other organic structure in a body with an elongated surgical instrument having an elongated movable rod therein extending from an outboard, proximal position to a distal end near a surgical site in said body, said surgical instrument carrying a plurality of surgical staple clips at said distal end of said rod, the method comprising the steps of:
- longitudinally moving said rod in a substantially singular, operative stroke;
during said single operative stroke:
- sequentially and pluralistically clipping said segment of blood vessel or other organic structure with a first group and then a second group of clips of said plurality surgical staple clips at different times during a first portion of said singular operative stroke; and
- subsequently cutting said segment of blood vessel or other organic structure during a second portion of said singular operative stroke.

27. A method for surgically stapling and cutting as claimed in claim 26 wherein said first group of clips is at least one clip and said second group of clips is one of a subplurality of clips and a remaining plurality of clips wherein said first group of clips is placed on said blood vessel or other organic structure before said second group of clips and both said first and second group of clips is placed on said blood vessel or other organic structure before said blood vessel or other organic structure is cut.

28. A method as claimed in claim 27 wherein said singular operative stroke is caused by a single, generally uniform extension of said rod towards said distal end.

29. A method as claimed in claim 28 wherein said surgical instrument defines a common axis at said distal end and wherein said clipping and cutting steps include the step of translating said singular longitudinal movement of said rod into sequential plural pivotal movements about said common axis.

30. A method as claimed in claim 29 wherein said surgical staple clips are generally U-shaped and the method includes the step of sequentially collapsing said U-shaped clips onto said segment during said first portion of said operative stroke.

* * * * *